(12) United States Patent
Shinya et al.

(10) Patent No.: US 7,470,714 B2
(45) Date of Patent: *Dec. 30, 2008

(54) GM-95-CONTAINING ANTITUMOR EFFECT POTENTIATOR, COMBINED ANTITUMOR PREPARATION AND ANTITUMOR AGENT

(75) Inventors: Kazuo Shinya, Tokyo (JP); Tetsuzo Tauchi, Kanagawa (JP); Toshiro Morohoshi, Tokyo (JP); Takashi Ono, Tokyo (JP)

(73) Assignee: Sosei Co., Ltd., Tokyo (JP)

( * ) Notice: Subject to any disclaimer, the term of this patent is extended or adjusted under 35 U.S.C. 154(b) by 159 days.

This patent is subject to a terminal disclaimer.

(21) Appl. No.: 10/547,541

(22) PCT Filed: Mar. 4, 2004

(86) PCT No.: PCT/JP2004/002746

§ 371 (c)(1),
(2), (4) Date: Sep. 1, 2005

(87) PCT Pub. No.: WO2004/078764

PCT Pub. Date: Sep. 16, 2004

(65) Prior Publication Data

US 2006/0167067 A1 Jul. 27, 2006

(30) Foreign Application Priority Data

Mar. 4, 2003 (JP) .............................. 2003-057632

(51) Int. Cl.
| | |
|---|---|
| *A01N 43/78* | (2006.01) |
| *A01N 43/04* | (2006.01) |
| *A01N 43/90* | (2006.01) |
| *A01N 43/54* | (2006.01) |
| *A01N 43/64* | (2006.01) |
| *A61K 31/425* | (2006.01) |
| *A61K 31/70* | (2006.01) |
| *A61K 31/00* | (2006.01) |
| *A61K 31/522* | (2006.01) |
| *A61K 31/515* | (2006.01) |
| *A61K 31/41* | (2006.01) |

(52) U.S. Cl. .................. 514/366; 514/15; 514/34; 514/251; 514/263.32; 514/269; 514/383; 514/492; 424/85.2; 424/85.4; 424/649

(58) Field of Classification Search .................. None
See application file for complete search history.

(56) References Cited

U.S. PATENT DOCUMENTS 6,613,759 B1 * 9/2003 Seto et al. .................. 514/183

2003/0166660 A1 9/2003 Tauchi
2003/0191165 A1 * 10/2003 Seto et al. .................. 514/366

FOREIGN PATENT DOCUMENTS

| EP | 1 123 937 A1 | 8/2001 |
| JP | 11-228451 A | 8/1999 |
| WO | WO-00/24747 A1 | 5/2000 |

OTHER PUBLICATIONS

Shin-ya et. al., J.Amer.Chem.Soc., 123(6), 1262-1263.*
Cecil Textbook of Medicine, 21st Edition (2000), Goldman & Bennett (Editors), W.B. Saunders Company (Publisher), Chapter 198, pp. 1060-1074.*
Internal Medicine, 4th Edition, Editor-in-Chief Jay Stein, Chapters 71-72, pp. 699-715.*
Tauchi, Tetsuzo et al., Blood; Journal of the American Society of Hematology, Nov. 16, 2001, vol. 98, No. 11, part 1, 616a.
Murakami, J. et al., European Journal of Cancer 1999, vol. 35, No. 6, pp. 1027-1034.

* cited by examiner

*Primary Examiner*—James O. Wilson
*Assistant Examiner*—Jeffrey H Murray
(74) *Attorney, Agent, or Firm*—Birch, Stewart, Kolasch & Birch, LLP

(57) ABSTRACT

An antitumor effect enhancer for enhancing the antitumor effects of an antitumor substance, which comprises a compound represented by the following formula (1):

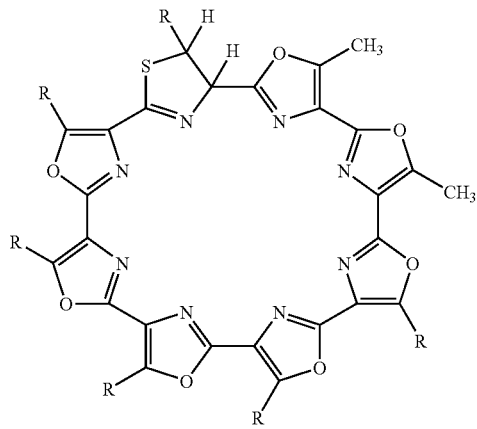

(1)

wherein each R independently represents a hydrogen atom, a lower alkyl group, an aryl group, an allyl group, an aralkyl group, a halogen atom, a hydroxyl group, an amino group, R'O—, R'(C=O)—, R'(C=O)O—, or R'O(C=O)—, wherein R' is an alkyl group containing 1 to 5 carbon atoms, or a pharmaceutically acceptable salt thereof.

6 Claims, 20 Drawing Sheets

GM-95-CONTAINING ANTITUMOR EFFECT POTENTIATOR, COMBINED ANTITUMOR PREPARATION AND ANTITUMOR AGENT

TECHNICAL FIELD

The present invention relates to an antitumor preparation in which two or more compounds having antitumor action are used in combination. More specifically, the present invention relates to an antitumor preparation in which an antitumor compound having multiple oxazole rings and another antitumor substance are used in combination.

BACKGROUND ART

Tumor cells (cancer cells) have a higher proliferation rate than that of normal cells. When the effect of killing tumor cells is equivalent to or lower than the proliferation rate of the tumor cells, it can only suppress progression of the cancer, and thus it cannot constitute a radical cancer treatment. In addition, each antitumor agent has its own optimal dosage. Even if an antitumor agent is administered at an amount larger than such optimal dosage, the effect of killing tumor cells does not proportionally increase, but in general, the effect increases by only a slight extent. Moreover, when a large amount of antitumor agent is administered, adverse effects such as damage to normal cells appear rather strongly in many cases. Thus, it is hardly anticipated that a great therapeutic effect can be obtained by administration of a single type of antitumor agent in large amounts.

Under the aforementioned circumstances, in order to improve antitumor effects and reduce side effects, or in order to prevent tumor cells from obtaining resistance to drugs, multi-drug combination therapy in which two or more types of agents are used in combination is often conducted.

In recent years, telomerase has become a focus of attention as a cancer molecule target. Telomerase is not expressed in normal cells except for several tissues, but it is reexpressed at a high frequency in 90% or more of cancer cells. The length of telomerase is closely associated with the aging of cells. Accordingly, it is anticipated that such aging of cancer cells is artificially caused by treating them with a telomerase inhibitor. 40% of the agents that are currently used in clinical sites are compounds derived from nature, such as microbial metabolites. Such compounds derived from nature are still widely used as sources for the development of agents.

The present inventors have found that Actinomyces isolated from the soil (the 3533-SV4 strain, belonging to the genus *Streptomyces*) produces an antitumor compound having multiple oxazole rings (hereinafter referred to as "the GM-95 substance" at times). The inventors have already reported the details thereof (refer to International Publication WO00/24747, for example). The GM-95 substance is the strongest telomerase inhibitor among telomerase inhibitors including synthetic compounds that have been reported to date. The action of the GM-95 substance on several types of cancer cells was analyzed. As a result, it was found that the GM-95 substance induces the aging of cells, which is attended with telomere shorting. In addition, the aged cells had lost their tumorigenicity. These results suggested the possible use of the GM-95 substance as an antitumor agent.

However, nothing has been known regarding an antitumor pharmaceutical in which a telomerase inhibitor such as the GM-95 substance and another antitumor substance are used in combination, or regarding the effects obtained from such combined use.

(Patent Document 1) International Publication WO00/24747

DISCLOSURE OF THE INVENTION

It is an object of the present invention to synergistically enhance antitumor action by the combined use of two or more types of antitumor substances and to provide a combined antitumor agent, the antitumor action of which has been enhanced synergistically.

As a result of intensive studies directed towards achieving the aforementioned object, the present inventors have found that when a GM-95 substance or a derivative thereof is used in combination with another antitumor substance, the obtained antitumor activity becomes significantly higher than that obtained when such substances are used singly, thereby completing the present invention.

That is to say, the present invention includes the following features.

(1) An antitumor effect enhancer, which comprises a compound represented by the following formula (1):

$$(1)$$

wherein each R independently represents a hydrogen atom, a lower alkyl group, an aryl group, an allyl group, an aralkyl group, a halogen atom, a hydroxyl group, an amino group, R'O—, R'(C=O)—, R'(C=O)O—, or R'O(C=O)—, wherein R' is an alkyl group containing 1 to 5 carbon atoms, or a pharmaceutically acceptable salt thereof.

(2) The antitumor effect enhancer according to (1) above, wherein the antitumor substance is selected from the group consisting of an alkylating agent, an antimetabolite, an antitumor antibiotic, a microtubule inhibitor, a hormone agent, a platinum complex, a topoisomerase inhibitor, a biologic, and a molecule-targeting therapeutic agent.

(3) The antitumor effect enhancer according to (1) above, wherein the antitumor substance is selected from the group consisting of a mustard agent, a nitrosourea compound, a folic acid compound, a pyrimidine compound, a purine compound, an anthracycline compound, vinca alkaloid, taxane, an antiestrogen agent, an LH-RH agonist, a topoisomerase type I inhibitor, a topoisomerase type II inhibitor, interferon, interleukin, a molecule-targeting therapeutic agent, Cisplatin, Carboplatin, and Nedaplatin.

(4) The antitumor effect enhancer according to any one of (1) to (3) above, which is used for treatment of a disease selected from the group consisting of head and/or neck cancer, esophageal cancer, stomach cancer, colon cancer, rectal cancer, liver cancer, gallbladder and/or bile duct cancer, pancreatic cancer, kidney cancer, lung cancer, breast cancer, ovarian cancer, bladder cancer, prostatic cancer, orchioncus, osteosarcoma and/or soft part sarcoma, cervix cancer, skin cancer, encephaloma, malignant lymphoma, and leukemia.

(5) A combined antitumor preparation, which uses a compound represented by the following formula (1):

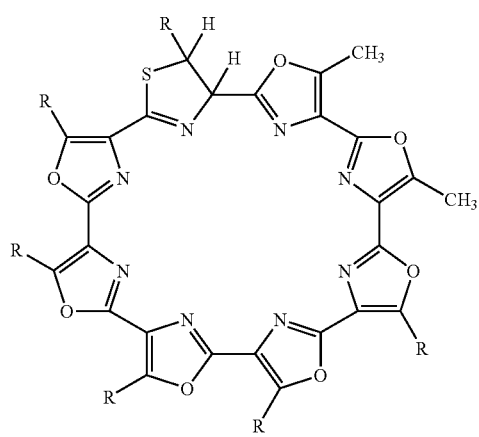

(1)

wherein each R independently represents a hydrogen atom, a lower alkyl group, an aryl group, an allyl group, an aralkyl group, a halogen atom, a hydroxyl group, an amino group, R'O—, R'(C=O)—, R'(C=O)O—, or R'O(C=O)—, wherein R' is an alkyl group containing 1 to 5 carbon atoms, or a pharmaceutically acceptable salt thereof in combination with another antitumor substance, for simultaneously, separately, or successively administering the compound represented by the formula (1) and the other antitumor substance.

(6) The combined antitumor preparation according to (5) above, wherein the antitumor substance is selected from the group consisting of an alkylating agent, an antimetabolite, an antitumor antibiotic, a microtubule inhibitor, a hormone agent, a platinum complex, a topoisomerase inhibitor, a biologic, and a molecule-targeting therapeutic agent.

(7) The combined antitumor preparation according to (5) above, wherein the antitumor substance is selected from the group consisting of a mustard agent, a nitrosourea compound, a folic acid compound, a pyrimidine compound, a purine compound, an anthracycline compound, vinca alkaloid, taxane, an antiestrogen agent, an LH-RH agonist, a topoisomerase type I inhibitor, a topoisomerase type II inhibitor, interferon, interleukin, a molecule-targeting therapeutic agent, Cisplatin, Carboplatin, and Nedaplatin.

(8) The combined antitumor preparation according to any one of (5) to (7) above, which is used for treatment of a disease selected from the group consisting of head and/or neck cancer, esophageal cancer, stomach cancer, colon cancer, rectal cancer, liver cancer, gallbladder and/or bile duct cancer, pancreatic cancer, kidney cancer, lung cancer, breast cancer, ovarian cancer, bladder cancer, prostatic cancer, orchioncus, osteosarcoma and/or soft part sarcoma, cervix cancer, skin cancer, encephaloma, malignant lymphoma, and leukemia.

(9) An antitumor agent, which uses a compound represented by the following formula (1):

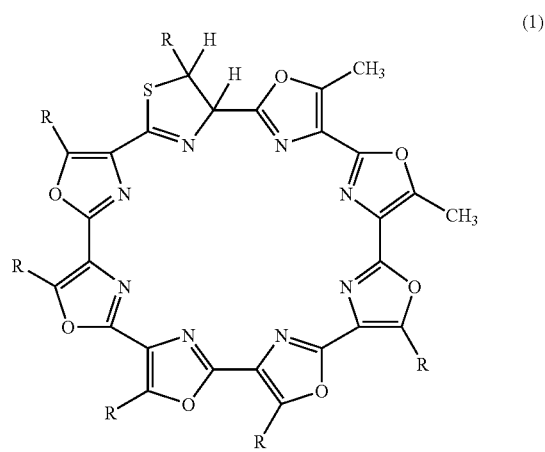

(1)

wherein each R independently represents a hydrogen atom, a lower alkyl group, an aryl group, an allyl group, an aralkyl group, a halogen atom, a hydroxyl group, an amino group, R'O—, R'(C=O)—, R'(C=O)O—, or R'O(C=O)—, wherein R' is an alkyl group containing 1 to 5 carbon atoms, or a pharmaceutically acceptable salt thereof in combination with another antitumor substance.

(10) The antitumor agent according to (9) above, wherein the antitumor substance is selected from the group consisting of an alkylating agent, an antimetabolite, an antitumor antibiotic, a microtubule inhibitor, a hormone agent, a platinum complex, a topoisomerase inhibitor, a biologic, and a molecule-targeting therapeutic agent.

(11) The antitumor agent according to (9) above, wherein the antitumor substance is selected from the group consisting of a mustard agent, a nitrosourea compound, a folic acid compound, a pyrimidine compound, a purine compound, an anthracycline compound, vinca alkaloid, taxane, an antiestrogen agent, an LH-RH agonist, a topoisomerase type I inhibitor, a topoisomerase type II inhibitor, interferon, interleukin, a molecule-targeting therapeutic agent, Cisplatin, Carboplatin, and Nedaplatin.

(12) The antitumor agent according to any one of (9) to (11) above, which is used for treatment of a disease selected from the group consisting of head and/or neck cancer, esophageal cancer, stomach cancer, colon cancer, rectal cancer, liver cancer, gallbladder and/or bile duct cancer, pancreatic cancer, kidney cancer, lung cancer, breast cancer, ovarian cancer, bladder cancer, prostatic cancer, orchioncus, osteosarcoma and/or soft part sarcoma, cervix cancer, skin cancer, encephaloma, malignant lymphoma, and leukemia.

(13) A telomerase inhibitor, which comprises a compound represented by the following formula (1):

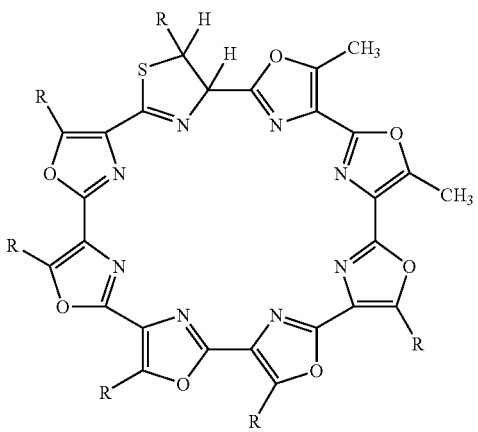

wherein each R independently represents a hydrogen atom, a lower alkyl group, an aryl group, an allyl group, an aralkyl group, a halogen atom, a hydroxyl group, an amino group, R'O—, R'(C=O)—, R'(C=O)O—, or R'O(C=O)—, wherein R' is an alkyl group containing 1 to 5 carbon atoms, or a pharmaceutically acceptable salt thereof, and another antitumor substance.

A compound used in the present invention is represented by the following formula (1):

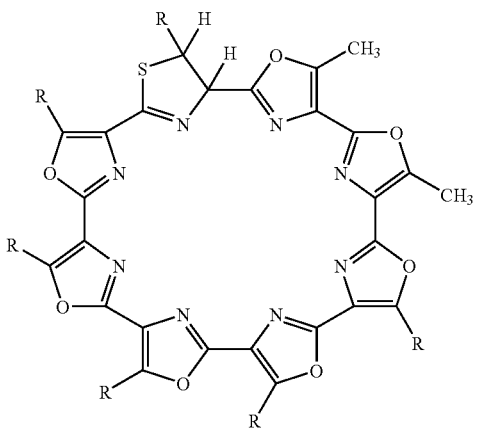

wherein each R independently represents a hydrogen atom, an alkyl group containing 1 to 5 carbon atoms, an aryl group, an aralkyl group, a heteroaryl group, a halogen atom, a hydroxyl group, an amino group, R'O—, R'(C=O)—, R'(C=O)O—, or R'O(C=O)—, wherein R' is an alkyl group containing 1 to 5 carbon atoms.

The term "alkyl group containing 1 to 5 carbon atoms" is used in the present specification to mean lower alkyl such as a methyl group, an ethyl group, a propyl group, an isopropyl group, an n-butyl group, a sec-butyl group, a tert-butyl group, or an isobutyl group.

More specifically, the following groups are exemplified as substituent R. Examples of an aryl group may include a phenyl group and a naphthyl group. An example of an aralkyl group may be a benzyl group. Examples of a heteroaryl group may include: nitrogen-containing aromatic groups such as an imidazolyl group or a pyridinyl group; sulfur-containing aromatic groups such as thiophene or thiazole; and oxygen-containing aromatic groups such as furan or oxazole. Examples of a halogen atom may include a fluorine atom, a chlorine atom, a bromine atom, and an iodine atom.

Examples of a pharmaceutically acceptable salt of the compound represented by formula (1) may include acid-added salts including inorganic acid salts such as hydrochloride, sulfate, or phosphate, and organic acid salts such as acetate, maleate, fumarate, tartrate, citrate, or lactate.

Hereinafter, the compound represented by formula (1) or a pharmaceutically acceptable salt thereof may be referred to as "Telomestatin" at times in the present specification.

A compound wherein, in the above formula (1), all the Rs are hydrogen atoms is called the "GM-95 substance" or "Telomestatin (TMS)." The physicochemical properties of the GM-95 substance are described below.

1) Molecular formula: The measurement value (M+H) was 583.0790 in the measurement by high-resolution fast atomic bombardment mass spectrometry. The molecular formula corresponding to this measurement value is C26H15N8O7S.

2) Molecular weight: The molecular weight was 582.0712 in the measurement by fast atomic bombardment mass spectrometry.

3) Melting point: 138° C. to 143° C. (decomposition)

4) Specific rotation: The specific rotation was measured at a concentration of C=0.129 g/100 ml (methanol) in methanol. [α]D20=−9.38°

5) Ultraviolet absorption spectrum: as shown in FIG. 1

The measurement was carried out in methanol (7.39 μM solution). The maximum absorption was obtained at 259.5 nm, and the absorbance was 0.288 at that time. The molar absorption coefficient (ε) was 38982.

6) Infrared absorption spectrum (FT-IR): as shown in FIG. 2
νmax (cm$^{-1}$): 3421, 3147, 2958, 2923, 2854, 1733, 1670, 1650, 1544, 1496, 1438, 1392, 1351, 1315, 1267, 1199, 1174, 1118, 1087, 1058, 1033, 975, 943, 929, 914, 883, 798

7) Solubility in solvents: The GM-95 substance is insoluble in water and acetone. It is soluble in a mixture consisting of chloroform and methanol (1:1).

8) Color of the substance: White yellowish powders

9) Nuclear magnetic resonance spectrum

The chemical shift of the 500 MHz $^1$H-NMR spectrum (shown in FIG. 3) and that of the 125 MHz $^{13}$C-NMR spectrum (shown in FIG. 4), which were measured at 25° C. in a solution consisting of heavy chloroform and heavy methanol (1:1), are shown below.

TABLE 1

(1)

| Carbon position | $^{13}$C-NMR | $^1$H-NMR |
|---|---|---|
| 1 | 162.5 | |
| 2 | 150.5 | |
| 3 | 125.1 | |
| 4 | 155.4 | |

TABLE 1-continued

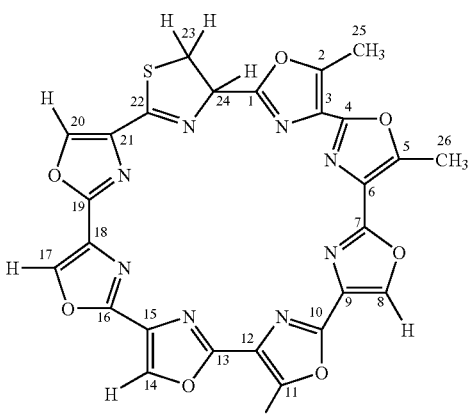

(1)

| Carbon position | $^{13}$C-NMR | $^1$H-NMR |
|---|---|---|
| 5 | 149.6 | |
| 6 | 126.0 | |
| 7 | 157.3 | |
| 8 | 137.8 | 8.17 (s, 1H) |
| 9 | 130.4 | |
| 10 | 156.8 | |
| 11 | 138.8 | 8.24 (s, 1H) |
| 12 | 130.7 | |
| 13 | 156.2 | |
| 14 | 141.2. | 8.00 (s, 1H) |
| 15 | 136.7 | |
| 16 | 156.6 | |
| 17 | 139.4 | 8.28 (s, 1H) |
| 18 | 130.9 | |
| 19 | 156.6 | |
| 20 | 138.1 | 8.18 (s, 1H) |
| 21 | 130.4 | |
| 22 | 160.0 | |
| 23 | 38.7 | 3.8 (m, 1H), 3.46 (m, 1H) |
| 24 | 73.2 | 6.19 (br s, 1H) |
| 25 | 11.5 | 2.47 (s, 3H) |
| 26 | 11.5 | 2.64 (s, 3H) |

10) Retention time (Rt) in high performance liquid chromatography (HPLC)

A peak was detected at 6.1 minutes under the following analytical conditions.

Column: PEGASIL ODS (inside diameter 4.6 mm×250 mm, manufactured by Senshu Scientific Co., Ltd.).
Mobile phase: acetonitrile/trifluoroacetic acid/water (70:0.1:30 V/V/V)
Flow rate: 1 ml/min.
Detection: 254 nm The GM-95 substance can be produced by culturing a strain having ability to produce the above substance (hereinafter referred to as "GM-95 substance-producing strain") under the following suitable conditions, for example.

Examples of such a GM-95 substance-producing strain may include strains belonging to the genus *Streptomyces*. Examples of such a strain belonging to the genus *Streptomyces* may include the *Streptomyces anulatus* 3533-SV4 strain and a mutant strain thereof. The *Streptomyces anulatus* 3533-SV4 strain is a strain belonging to the genus *Streptomyces*, which the present inventors have newly isolated from the soil at Tensui-machi, Tamana-gun, Kumamoto prefecture. This strain was deposited with the National Institute of Bioscience and Human-Technology, Agency of Industrial Science and Technology, at Higashi 1-1-3, Tsukuba, Ibaraki, Japan (the current National Institute of Advanced Industrial Science and Technology, an Independent Administrative Institution under the Ministry of Economy, Trade and Industry), as indication of microorganism (indication made by the depositor for identification): *Streptomyces anulatus* 3533-SV4 (GM95), under accession No. FERM BP-6460, on Aug. 12, 1998.

Identification of *Streptomyces anulatus* 3533-SV4 and determination of the mycological properties thereof were carried out in accordance with the method of ISP (International Streptomyces Project). The *Streptomyces anulatus* 3533-SV4 strain has the following mycological properties.

a) Form

The present strain was cultured on mediums of ISP No. 2, 3, 4, and 5, at 27° C. for 14 days. The results are shown below.
 1) Ramification in sporogenesis: Simple ramification
 2) Form of sporogenesis: Spiral, the form of spores is tubular
 3) Number of spores: 10 to 50 or more
 4) Surface structure of spore: Smooth
 5) Size of spore: 0.3 to 0.5×0.7 to 1.0 µm
 6) Presence or absence of flagellar spores: Non
 7) Presence or absence of sporangia: Non
 8) Position to which sporophore adheres: Aerial hypha
 9) Presence or absence of sclerotium formation: Non B) Growing Conditions on Various Types of Mediums The Growing conditions of the present strain on various types of mediums are shown in Table 2. In the table, the color tones of mediums are expressed in accordance with "The Color Harmony Manual (1958)" published by Container Corporation of America.

Table 2

TABLE 2

| Medium | Color tone of aerial hypha | Color tone of substrate hypha | Diffusible pigment |
|---|---|---|---|
| Sucrose-nitrate agar | Yellow line | White yellow | Non |
| Glucose-asparagine agar | Yellow line | White yellowish brown/bright yellow | Non |
| Glycerin-asparagine agar | Yellow line | White yellow | Non |
| Inorganic salt-starch agar | Yellow line | Bright yellowish brown/white yellowish brown | Non |
| Tyrosine agar | Yellow line | Bright yellowish brown | White brown |
| Nutrient agar | Yellow line | White yellow | Non |
| Yeast-malt agar | Yellow line | White yellowish brown | Non |
| Oatmeal agar | Yellow line | White yellow/bright yellowish brown | Non | c) Physiological Properties
 1) Growth temperature range: 20° C. to 32° C.; Optimal temperature: 20° C. to 30° C.
 2) Liquefaction of gelatin: +
 3) Hydrolysis of starch: +
 4) Coagulation or peptonization of dried skim milk: +
 5) Generation of melanin-like pigments
  Tyrosine agar medium: −
  Peptone-yeast iron agar medium: −
  Tryptone-yeast-broth medium: +
 6) Reduction of nitrate: +
 7) Assimilation of carbon source (Pridham-Gottlieb agar medium (ISP No. 9))
  L-arabinose +; D-xylose +; D-glucose +; D-fructose +; sucrose +; inositol +; L-rhamnose +; raffinose +; D-mannite + d) Composition of Strain

The acid hydrolysate of the entire strain was analyzed by the thin-layer chromatography described in "*Hosenkin no dotei jikken ho*-6-2-70, 1985 (Methods for identification of Actinomycetes-6-2-70, 1985)" edited by the Society for Actinomycetes Japan. As a result, LL-diaminopimelic acid was detected.

The substrate hypha of the present strain does not branch off. The aerial hypha thereof forms a long main axis. A 4- to 9-times-rotated spiral spore chain consisting of 10 to 50 or more spores is formed at the tip of a branch that is irregularly branched from the main axis. Such a spore is nonmotile and has a cylindrical or elliptic form. It has a width between 0.3 and 0.5 μm and a length between 0.7 and 1.0 μm. Its surface is smooth. No particular items such as sclerotium or sporangium are observed. The chemotype of the cell wall is type (I). Culture properties thereof are shown in Table 2. The color tone of aerial hypha is a yellow line. The color tone of substrate hypha is unclear, and it does not change depending on pH. No diffusible pigments are observed in the strain as a whole. Physiological properties thereof are described in c) above. The present strain is mesophilic. Taking into consideration the morphological properties of the present strain and the chemotype of the cell wall thereof, the present strain is considered to belong to the genus *Streptomyces* (hereinafter abbreviated as "S.").

Based on the aforementioned properties, the species belonging to the genus S. described in "Approval list of nomenclature of bacteria, 1980" and the following valid name lists have been searched, so as to select related species. When the diagnostic properties of *S. spheroides* are compared with those of the present strain, it is found that the properties of the present strain are very similar to those of *S. spheroides*, but that they are different in terms of only assimilation of carbon source.

Accordingly, the present strain is a new strain that is the most similar to *S. spheroides*. However, Williams et al. have described in Bergey's Manual of Systematic Bacteriology, Vol. 4 that *S. spheroides* is a synonym of *S. anulatus*. Accordingly, the present 3533-SV4 strain is identified as a strain included in *S. anulatus*, and it is referred to as the *Streptomyces anulatus* 3533-SV4 strain.

A comparison between the present strain and the related species is shown below.

Table 3

TABLE 3

|  |  | The present strain 3533-SV4 | *Streptomyces spheroids* |
|---|---|---|---|
| Spore chain form | Spiral | + | + |
| Spore surface | Smooth | + | + |
| Color tone of aerial hypha | Yellow | + | + |
| Color tone of substrate hypha | Unclear | + | + |
| pH sensitivity |  | − | − |
| Diffusible pigment generation |  | − | − |
| Melanin pigment generation |  | − | − |
| Starch hydrolysis |  | + | + |
| Nitrate reduction |  | + | + |
| Growth temperature | 10° C. | − | − |
|  | 45° C. | − | − |
| Carbon assimilation |  |  |  |
| Arabinose |  | + | − |
| Xylose |  | + | + |
| Inositol |  | + | − |
| Mannitol |  | + | + |
| Rhamnose |  | + | + |

TABLE 3-continued

|  | The present strain 3533-SV4 | *Streptomyces spheroids* |
|---|---|---|
| Raffinose | + | − |
| Sucrose | + | + |
| Fructose | + | + |

The GM-95 substance can be produced, for example, by culturing various types of GM-95 substance-producing strains belonging to the genus *Streptomyces*, such as the aforementioned 3533-SV4 strain or a mutant strain thereof having the aforementioned mycological properties, in a suitable medium, and then separating a crude extract containing the substance of the present invention from the culture solution, followed by isolation and purification of the GM-95 substance from the obtained crude extract. The culture solution contains a culture filtrate and strain solids.

In principle, the culture of the aforementioned microorganisms is carried out in accordance with a common culture of microorganisms. In general, such culture is preferably carried out under aerobic conditions according to the shaking culture method involving liquid culture or the aeration-agitation culture method. Any type of medium can be used for the culture, as long as it contains a source of nutrient that can be used by GM-95 substance-producing strains. Various types of synthetic mediums and natural mediums can be used. Examples of a carbon source for medium may include glucose, sucrose, fructose, glycerin, dextrin, starch, molasses, corn steep liquor, and organic acid. These carbon sources can be used singly or in combination with two or more types. Examples of a nitrogen source may include: organic nitrogen sources such as pharma media, peptone, meat extract, yeast extract, soy flour, casein, amino acid, or urea; and inorganic nitrogen sources such as sodium nitrate or ammonium sulfate. These nitrogen sources can be used singly or in combination with two or more types. In addition, sodium salts, potassium salts, magnesium salts, phosphate, other heavy metal salts, or the like, are appropriately added to the medium, as necessary.

When significant foaming is observed during the culture, antifoaming agents including vegetable oils such as soybean oil or linseed oil, higher alcohols such as octadecanol, tetradecanol, or heptadecanol, or various types of silicon compounds may appropriately be added to the medium.

The pH of the medium is preferably around neutral. The culture temperature may be maintained at a temperature at which the GM-95 substance-producing strains grow favorably. Thus, the culture temperature is maintained generally between 20° C. and 32° C., and particularly preferably between 25° C. and 30° C. The culture time is preferably approximately between 2 and 6 days in both cases of liquid shaking culture and aeration-agitation culture.

The aforementioned various culture conditions can appropriately be changed depending on the type of microorganisms used, the properties thereof, external conditions, and so on. In addition, the optimal culture conditions can appropriately be selected from the aforementioned range and adjusted, depending on the aforementioned conditions.

A crude extract containing the GM-95 substance can be separated from the culture solution according to a common method of collecting fermented products. For example, common means such as solvent extraction, chromatography, or crystallization can be used singly or in combination with two or more types in any given order.

More specifically, the following method can be used. That is to say, since the GM-95 substance produced by the aforementioned culture mainly exists in a culture filtrate and strain solids, the culture solution is first subjected to filtration, centrifugation, or the like, according to common methods, so as to separate the strain solids from the culture filtrate. Thereafter, the GM-95 substance is eluted from the obtained strain solids containing the GM-95 substance, using solvents such as methanol or acetone. Subsequently, the solvent is distilled away under a reduced pressure, so as to obtain a crude concentrate containing the GM-95 substance. An organic solvent that does not mix with water, such as ethyl acetate, chloroform, or butanol, was added to the crude concentrate, so as to dissolve the GM-95 substance in the organic solvent layer. Thereafter, salt cake was added to the obtained solvent layer and dehydrated. The solvent is then distilled away under a reduced pressure, so as to obtain a crude extract containing the GM-95 substance. In the case of a culture filtrate also, the same above operation to dissolve the GM-95 substance in an organic solvent layer is carried out, so as to obtain a crude extract. Moreover, by adjusting pH by addition of sodium hydroxide or hydrochloric acid, or by adding industrial salts to the reaction product, extraction efficiency can be increased, or generation of emulsion can be prevented, as necessary.

Furthermore, in order to isolate and purify the GM-95 substance from a crude extract, common means for isolating and purifying fat-soluble low molecular weight substances can be applied. Examples of such means may include: various types of adsorption chromatography using adsorbents such as activated carbon, silica gel, alumina, or macroporous non-ionic adsorption resin; and reverse phase chromatography using ODS bonded silica gel or the like. Of these, silica gel chromatography using, as an elution solvent, chloroform, or a mixed solvent consisting of chloroform/ethyl acetate, chloroform/methanol, chloroform/acetone, benzene/acetone, or the like, and reverse phase chromatography using a mixed solvent consisting of acetonitrile or methanol/0.05% trifluoroacetic acid or 10 mM monopotassium phosphate for elution, are particularly preferable. In addition, when further purification is required, the aforementioned chromatography is carried out repeatedly, or column chromatography using Sephadex LH-20 (manufactured by Pharmacia), in which chloroform or methanol is used as an elution solvent, is appropriately performed in combination of the aforementioned chromatography, so as to obtain a high-purity GM-95 substance.

In order to confirm the presence of the GM-95 substance during the purification process, a detection method involving thin-layer chromatography may be applied in combination with a detection method involving high performance liquid chromatography.

Moreover, applying a known chemical synthesis technique or the like, other Telomestatins (for example, a compound wherein, in formula (1), each R represents a hydrogen atom, a lower alkyl group, an aryl group, an allyl group, an aralkyl group, a halogen atom, a hydroxyl group, an amino group, R'O—, R'(C=O)—, R'(C=O)O—, or R'O(C=O)—, wherein R' is an alkyl group containing 1 to 5 carbon atoms) can easily be obtained from the aforementioned GM-95 substance.

It has been found that Telomestatin used in the present invention has extremely strong telomerase inhibitory activity. Such Telomestatin is useful as an antitumor agent having a wide spectrum regarding inhibition of the activity of the above enzyme. For example, according to a common method, the GM-95 substance was subjected to a telomerase inhibitory activity test, in which a cell extract containing telomerase was used. The concentration necessary for inhibiting 50% of telomerase activity in the cell extract (IC50) was obtained. As a result, IC50 was found to be 50 nM. Telomerase hardly exists in normal cells, but it exists in a wide range of malignant tumors. (Telomerase was observed in 85% or more of all the malignant tumors including tumor cell lines found in the skin, breast, lung, stomach, pancreas, ovary, neck, uterus, kidney, bladder, colon, prostate, central nerve system (CNS), retina, and blood.)

As a result of the studies of the present inventors, it was found that when such Telomestatin is used in combination with another antitumor substance, the obtained antitumor activity becomes significantly higher than that obtained when such substances are used singly. That is to say, when such Telomestatin represented by formula (1) is used in combination with another antitumor substance, it becomes useful for synergistically enhancing their antitumor effects.

The antitumor effect enhancer of the present invention containing Telomestatin can be administered, before or after administration of another antitumor substance, or simultaneously. When the above enhancer and another antitumor substance are simultaneously administered, a mixed preparation comprising another antitumor substance as well as the antitumor effect enhancer of the present invention may be produced, for example.

Moreover, Telomestatin represented by formula (1) may also be administered in the form of a combined antitumor preparation or a combined agent used together with an antitumor agent, which uses Telomestatins represented by formula (1) and another antitumor substance in combination.

The term "combined agent" is used in the present specification to mean not only a homogeneous mixture consisting of the Telomestatin represented by formula (1) and another antitumor substance, but also a combined use of each independent preparations for administration of the Telomestatin represented by formula (1) and another antitumor substance, simultaneously, separately, or successively (use and/or administration). Accordingly, the combined antitumor preparation and antitumor agent of the present invention may be used, either in the form of a homogeneously mixed preparation consisting of Telomestatin and another antitumor substance, or in the form of a combined preparation, in which each different preparations have been prepared in order to be administered separately.

The type of another antitumor substance that can be used in the present invention is not particularly limited, and any type of substance can be used as long as it generally has antitumor activity. Antitumor substances are classified into various types, depending on chemical structure, action mechanism, origin, or the like. They are broadly classified into alkylating agent-type compounds, antimetabolite-type compounds, plant alkaloid-type compounds, antitumor antibiotic-type compounds, platinum complex-type compounds, hormone agent-type compounds, and antitumor compounds other than the aforementioned compounds. Specific examples may include the below-mentioned compounds and salts thereof (acid-added salts such as hydrochloride or sulfate, or metal salts such as alkali metal salts).

Examples of an alkylating agent-type antitumor compound may include Cyclophosphamide, Ifosfamide, Melphalan, Busulfan, and Carboquone.

Examples of an antimetabolite-type antitumor compound may include a folate metabolism antagonist, a purine metabolism antagonist, and a pyrimidine metabolism antagonist. More specific examples may include 6-Mercaptopurine, Methotrexate, 5-Fluorouracil, Tegafur, Enocitabine, and Cytarabine.

Examples of a microtubule inhibitor-type antitumor compound may include vinca alkaloids, podophyllins, and taxanes. More specific examples may include Vincristine, Vindesine, and Vinblastine.

Examples of an antibiotic-type antitumor compound may include Actinomycin D, Daunorubicin, Bleomycin, Peplomycin, Mitomycin C, Aclarubicin, Neocarzinostatin, Doxorubicin, and Epirubicin.

Examples of a platinum complex-type antitumor compound may include Cisplatin, Carboplatin, and Nedaplatin.

Examples of a topoisomerase inhibitor may include a topoisomerase type I inhibitor, a topoisomerase type II inhibitor, Irinotecan, Nogitecan, Etoposide, and Daunorubicin.

Examples of antitumor substances other than those as described above may include Nimustine, L-Asparaginase, Procarbazine, a hormone agent, a biologic, a molecule-targeting therapeutic agent, a mustard agent, a nitrosourea compound, an anthracycline compound, vinca alkaloid, an antiestrogen agent, an LH-RH agonist, interferon, and interleukin.

In the present invention, platinum complex-type antitumor compounds, topoisomerase inhibitors, and antibiotic-type antitumor compounds are preferable as antitumor substances that are used in combination with the compound represented by formula (1). Of these, an anthracycline antitumor compound, a topoisomerase type I inhibitor, a topoisomerase type II inhibitor, and a platinum complex-type antitumor compound are particularly preferable. The weight ratio between the compound represented by formula (1) and another antitumor substance depends on the type of the antitumor substance used in combination, or the symptoms of a patient. It is generally between 1:1 and 1:100, and preferably between 1:1 and 1:10.

As a pharmaceutical dosage form of the preparation of the present invention such as an antitumor effect enhancer, a combined antitumor preparation, or an antitumor agent, various types of pharmacological dosage forms can be adopted depending on purpose. Examples of such a dosage form may include: oral agents such as a tablet, a capsule, a powder, a granule, a parvule, a solution, a pill, or an emulsion; and parenteral agents such as an injection, a suppository, an ointment, a plaster, an adhesive preparation, an aerosol, and an eye drop. The preparation of the present invention can be processed into these dosage forms by production methods that have been well known to persons skilled in the art.

When an oral solid preparation is produced, an excipient, and as necessary, a binder, a disintegrator, a lubricant, a coloring agent, a flavoring agent, a corrective, or the like are added to an active ingredient (that is, Telomestatin and/or the aforementioned another antitumor substance), and thereafter, a tablet, a capsule, a powder, a granule, a parvule, or the like can be produced from the obtained mixture according to common methods. Examples of an excipient used herein may include lactose, sucrose, starch, talc, magnesium stearate, crystalline cellulose, methylcellulose, carboxymethyl cellulose, glycerin, sodium alginate, and gum Arabic. Examples of a binder used herein may include polyvinyl alcohol, polyvinyl ether, ethylcellulose, gum Arabic, shellac, and saccharose. Examples of a disintegrator used herein may include dried starch, sodium alginate, agar powder, sodium bicarbonate, calcium carbonate, sodium lauryl sulfate, monoglyceride stearate, and lactose. Examples of a lubricant used herein may include magnesium stearate and talc. Examples of a flavoring agent may include saccharose, orange peel, citric acid, and tartaric acid. As other coloring agents or correctives, generally known products can be used. In addition, a tablet can be coated with a common coating agent according to known methods, as necessary. Examples of such a coated tablet may include a sugar-coated tablet, a gelatin-coated tablet, an enteric coated tablet, a film-coated tablet, a double-coated tablet, and a multiple layer tablet.

When an oral liquid preparation is produced, a flavoring agent, a buffer, a stabilizer, a corrective, or the like is added to an active ingredient, and thereafter, an oral liquid medicine, a syrup, an elixir, or the like can be produced from the obtained mixture. In this case, the aforementioned products can be used as flavoring agents. Sodium citrate or the like can be used as a buffer, and Tragacanth, gum Arabic, gelatin, or the like can be used as a stabilizer.

When an injection is produced, a diluent, a pH adjuster, a buffer, a stabilizer, an isotonizing agent, a local anesthetic, or the like is added to an active ingredient, and thereafter, intravenous, intramuscular, subcutaneous, intracutaneous, and intraperitoneal injections can be produced according to common methods. Examples of a diluent used herein may include water, ethyl alcohol, macrogol, propylene glycol, ethoxylated isostearyl alcohol, polyoxylated isostearyl alcohol, and polyoxyethylene sorbitan fatty acid esters. Examples of a pH adjuster and a buffer that can be used herein may include sodium citrate, sodium acetate, and sodium phosphate. Examples of a stabilizer used herein may include sodium pyrosulfite, ethylenediaminetetraacetic acid, thioglycolic acid, and thiolactic acid. Examples of an isotonizing agent used herein may include sodium chloride and glucose. Examples of a local anesthetic used herein may include procaine hydrochloride and lidocaine hydrochloride.

When a suppository is produced, a base material, and as necessary, a surfactant or the like, are added to an active ingredient, and thereafter, a suppository can be produced from the obtained mixture according to a common method. Examples of a base material used herein may include oil base materials such as macrogol, lanolin, cocoa butter, triglyceride-fatty acid, or Witepsol (manufactured by Dynamite Nobels).

When an ointment is produced, a commonly used base material, stabilizer, wetting agent, preservative, or the like are mixed with an active ingredient, as necessary, and these materials are blended according to a common method, so as to obtain a product. Examples of a base material used herein may include liquid paraffin, white petrolatum, white beeswax, octyldodecyl alcohol, and paraffin. Examples of a preservative used herein may include methyl parahydroxybenzoate, ethyl parahydroxybenzoate, and propyl parahydroxybenzoate.

When an adhesive preparation is produced, an active ingredient as well as the aforementioned ointment, cream, gel, paste, or the like may be applied to a common supporting medium according to a common method. Examples of a supporting medium used herein may include woven fabrics or nonwoven fabrics consisting of cotton, staple fibers, or chemical fibers, and films or a foam sheets that are made from soft vinyl chloride, polyethylene, polyurethane, or the like.

Furthermore, each of the aforementioned pharmaceutical preparations may comprise a coloring agent, a preservative, a perfume, a flavor, a sweetening agent, or the like, as necessary.

The amount of an active ingredient (that is, Telomestatin and/or the aforementioned another antitumor substance) contained in the preparation of the present invention is not particularly limited, and it is appropriately selected from a wide range. However, in general, such an active ingredient may be contained in such a preparation at a weight ratio between 1% and 70% by weight.

The administration method of the thus obtained preparation of the present invention is not particularly limited. It is appropriately determined depending on the forms of various types of preparations, the age, sex, or the like of a patient, the degree of the symptoms, and so on. For example, when a pharmaceutical preparation is administered in the form of an injection, it can be administered via intravenous, intramuscular, subcutaneous, intracutaneous, or intraperitoneal administration route. Such an injection may be mixed with a common complement fluid such as glucose or amino acid, and the mixed solution may be then administered intravenously. When the antitumor agent of the present invention has a solid form such as a tablet, a pill, a granule, or a capsule, or a liquid form for oral administration, it can be administered orally or enterally. A suppository can be administered into the rectum.

The amount of an active ingredient to be mixed into each of the above dosage forms can appropriately be determined depending on the symptoms of a patient to which the active ingredient is to be applied, or the dosage form. In general, in the case of an oral agent, the amount of an active ingredient is preferably approximately between 1 and 1,000 mg. In the case of an injection, it is preferably approximately between 0.1 and 500 mg, and in the case of a suppository, it is preferably approximately between 5 and 1,000 mg.

Moreover, the dosage per day of an agent having each of the above dosage forms is appropriately selected depending on the symptoms, body weight, age, or the like of a patient. The dosage of the agent per adult per day is generally approximately between 0.1 and 1,000 mg/kg, and preferably approximately between 1 and 100 mg/kg. Such dosage can be applied once or divided over 2 to 4 administrations per day.

The type of a tumor that can be treated by administration of the preparation of the present invention is not particularly limited. Examples of such a tumor may include: malignant solid tumors such as head and/or neck cancer, esophageal cancer, stomach cancer, colon cancer, rectal cancer, liver cancer, gallbladder and/or bile duct cancer, pancreatic cancer, kidney cancer, lung cancer, breast cancer, ovarian cancer, bladder cancer, prostatic cancer, orchioncus, osteosarcoma and/or soft part sarcoma, cervix cancer, skin cancer, or encephaloma; malignant lymphoma; and leukemia. Preferred examples are malignant solid tumors.

This specification includes part or all of the contents as disclosed in the specification and/or drawings of Japanese Patent Application No. 2003-057632, which is a priority document of the present application.

BEST MODE FOR CARRYING OUT THE INVENTION

Figure 1:
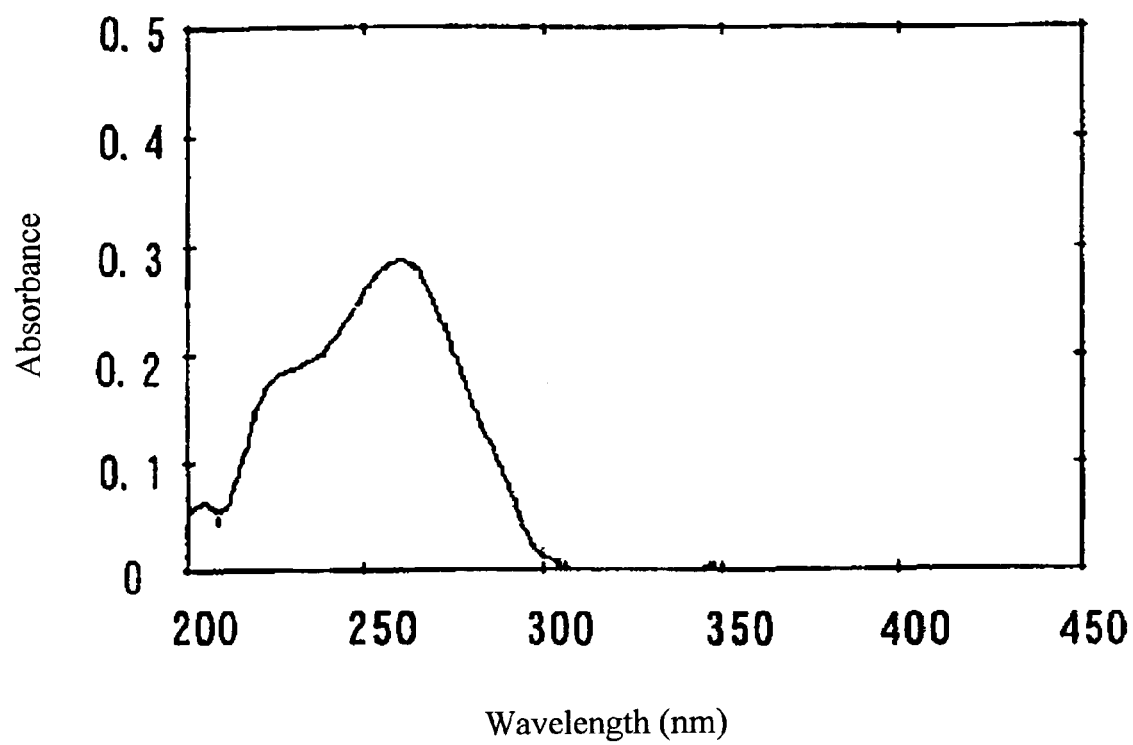
FIG. 1 shows an ultraviolet absorption spectrum of the GM-95 substance.

The present invention will be more specifically described below in the following examples. However, these examples are not intended to limit the scope of the present invention.

EXAMPLE 1

Production of GM-95 Substance (a) Culture Process 15 ml of a medium (pre-culture medium; pH 7.2) consisting of 1.0% soluble starch, 1.0% polypeptone, 1.0% molasses, and 1.0% beef extract was added to a test tube (50 ml), and it was then sterilized. After completion of the sterilization, a *Streptomyces anulatus* 3533-SV4 strain (FERM BP-6460) was inoculated into the medium at an amount of an inoculating loop, and the obtained mixture was subjected to shaking culture at 27° C. for 2 days on a reciprocal shaker.

Subsequently, 100 ml each of a medium (production medium; pH 7.2) consisting of 2.0% glycerin, 1.0% molasses, 0.5% casein, 0.1% polypeptone, and 0.4% calcium carbonate was dispensed into a 500-ml Erlenmeyer flask, and it was then sterilized (121° C., 15 minutes). Thereafter, the above strain was added to the sterilized medium at a ratio of 2% (v/v). The obtained mixture was subjected to rotary shaking culture at 27° C. for 3 days (220 rotations/min.; amplitude: 7 cm).

Subsequently, 30,000 ml each of the above medium was dispensed into three 50-L jar fermenters (Marubishi Physical and Chemical Research Institute). Thereafter, 15 ml of an antifoaming agent (Disfoam (CC-118); NOF Corporation), 15 ml of Shinetsu silicon (KM-68-2F; Shin-Etsu Chemical Co., Ltd.), and 15 ml of salad oil (Ajinomoto Co., Inc.) were added thereto, and the obtained mixture was then sterilized (120° C., 20 minutes). The aforementioned strain was added to the resultant product at a ratio of 2% (v/v), and the obtained mixture was cultured at 27° C. for 3 days (aeration-agitation: 400 rpm (agitation); 30 L/min. (aeration)).

(b) Separation Process 84.0 L of the culture solution obtained by the aforementioned procedures was collected, and cultured cells were then separated therefrom by centrifugation. The supernatant was discarded, and the cultured cells were extracted with 10.0 L of acetone for 2 hours, while being agitated sometimes. The extract was filtrated, and the filtrate was separated by repeatedly performing extraction with 5.0 L of acetone. Acetone extracts were gathered, and the gathered extract was concentrated to a final volume of 2 L by distillation. The solvent was distilled away under a reduced pressure, until acetone and water completely disappeared. The obtained oily residue was dissolved in 450 ml of methanol, and the solution was then filtrated. The obtained filtrate was evaporated to dryness under a reduced pressure.

(c) Isolation and Purification Process

The obtained oily residue was dissolved in 400 ml of a mixed solvent consisting of chloroform and methanol (20:1) (v/v). The obtained solution was subjected to a silica gel column (Wagogel C-200 (grain diameter: 75 to 150 µm), inside diameter: 6 cm×45 cm), and it was then eluted with 5 L of the same above chloroform-methanol mixed solvent. Fractions containing active substances were eluted with chloroform:methanol (10:1 v/v). Such fractions containing active substances were gathered, followed by evaporation to dryness under a reduced pressure. Subsequently, the roughly purified product was subjected to a silica gel column (grain diameter: 75 to 150 µm; inside diameter: 3.6 cm×30 cm), and it was then eluted with a mixed solvent consisting of chloroform, methanol, and 29% aqueous ammonia solution (700:100:1 v/v/v).

An eluant containing active substances was collected and then evaporated to dryness. The residue was dissolved in 10 ml of the aforementioned mobile phase, and the obtained solution was subjected to high performance liquid chromatography using a PEGASIL ODS column (Senshu Scientific Co., Ltd.; inside diameter: 20 mm×250 mm) (a mobile phase consisting of acetonitrile, trifluoroacetic acid, and water (70: 0.1:30 v/v/v); flow rate: 10.0 ml/min.; 254 nm (detection with 0.5 mm UV cell)). 0.8 ml of the extract was injected per once. Fractions containing the GM-95 substance were collected and then evaporated to dryness under a reduced pressure.

The residue was suspended in a 10% aqueous methanol solution, and the suspension was then subjected to a PEGASIL ODS column (Senshu Scientific Co., Ltd.; inside diameter: 1.0 cm×3 cm). It was washed with a 10% aqueous methanol solution, and then eluted with a 70% aqueous methanol solution. The obtained eluant was distilled away under a reduced pressure, so as to obtain 3.2 mg of the GM-95 substance.

Detection of a fraction containing the GM-95 substance was carried out at each stage of purification by high performance liquid chromatography using a PEGASIL ODS column (Senshu Scientific Co., Ltd.; inside diameter: 4.6 mm×250 mm) (a mobile phase consisting of acetonitrile, trifluoroacetic acid, and water (70:0.1:30 v/v/v); flow rate: 1.0 ml/min.).

The physicochemical properties of the GM-95 substance are described below.

1) Molecular formula: The measurement value (M+H) was 583.0790 in the measurement by high-resolution fast atomic bombardoment mass spectrometry. The molecular formula corresponding to this measurement value is $C_{26}H_{15}N_8O_7S$.
2) Molecular weight: The molecular weight was 582.0712 in the measurement by fast atomic bombardoment mass spectrometry.
3) Melting point: 138° C. to 143° C. (decomposition)
4) Specific rotation: The specific rotation was measured at a concentration of C=0.129 g/100 ml (methanol) in methanol.
   $[\alpha]D20=-9.38°$
5) Ultraviolet absorption spectrum: as shown in FIG. 1

The measurement was carried out in methanol (7.39 µM solution). The maximum absorption was obtained at 259.5 nm, and the absorbance was 0.288 at that time. The molar absorption coefficient ($\epsilon$) was 38982.

Figure 2:
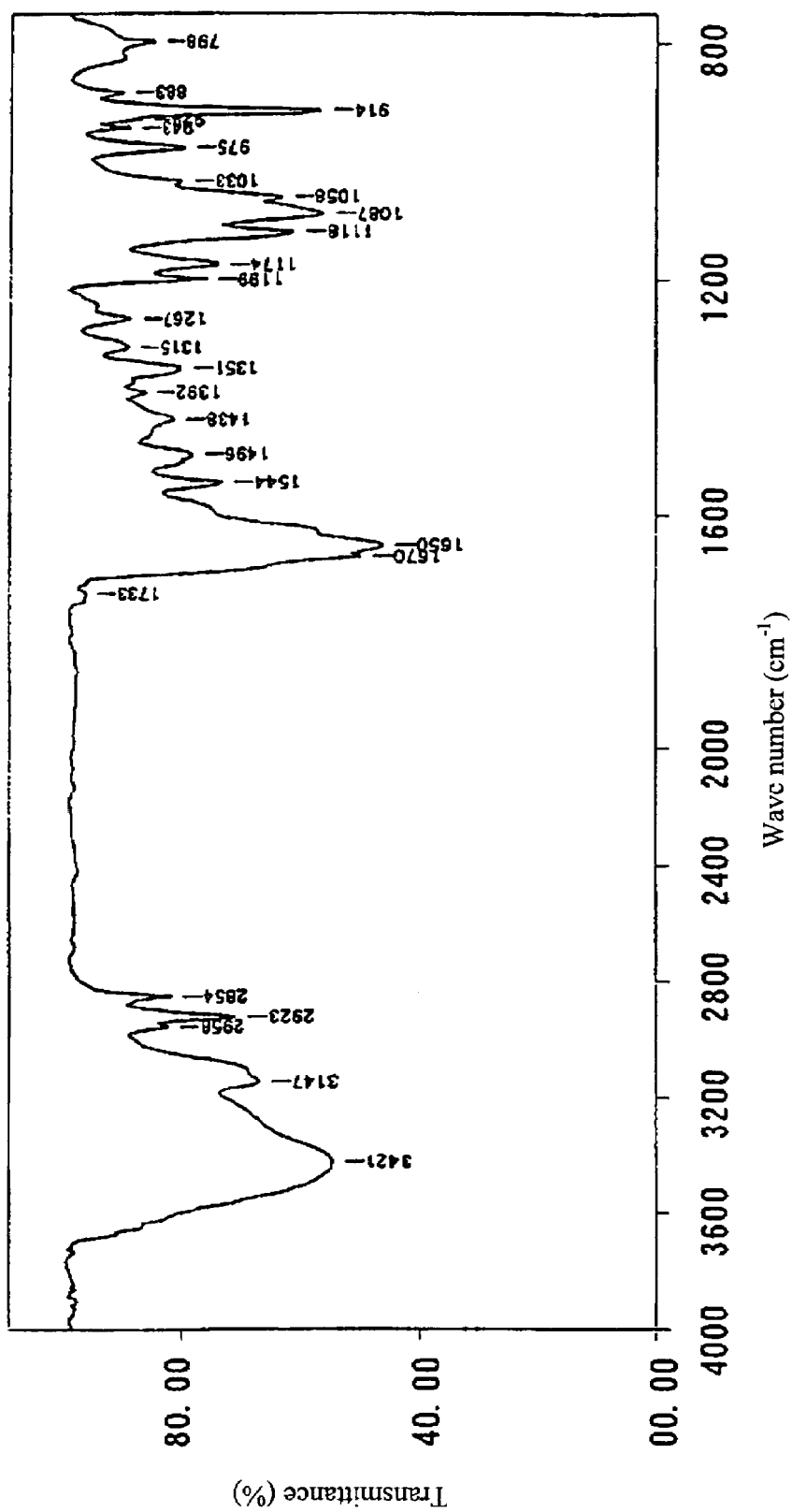
FIG. 2 shows an infrared absorption spectrum of the GM-95 substance.
Figure 3:
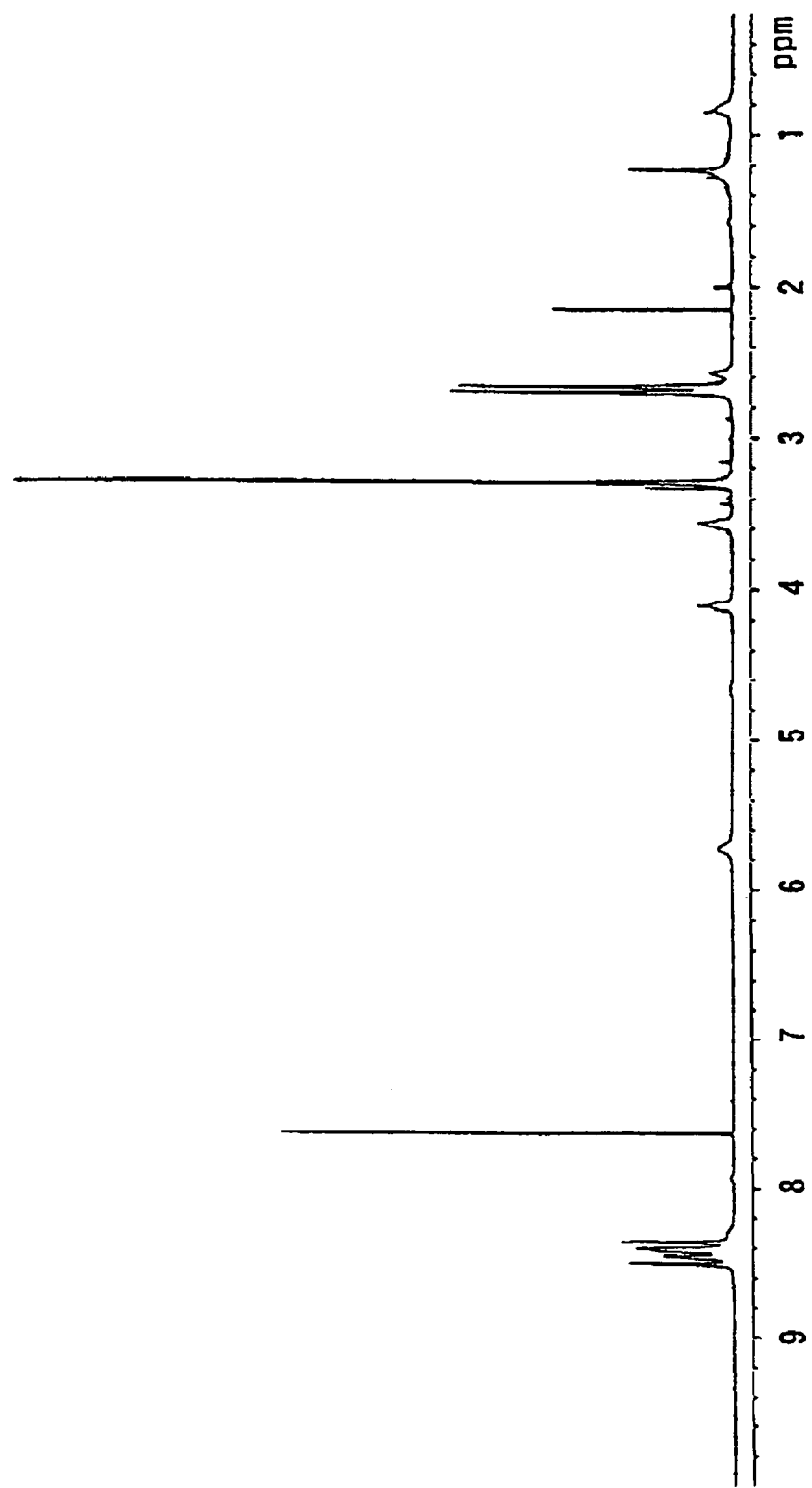
FIG. 3 shows a 500 MHz $^1$H-NMR spectrum of the GM-95 substance.
Figure 4:
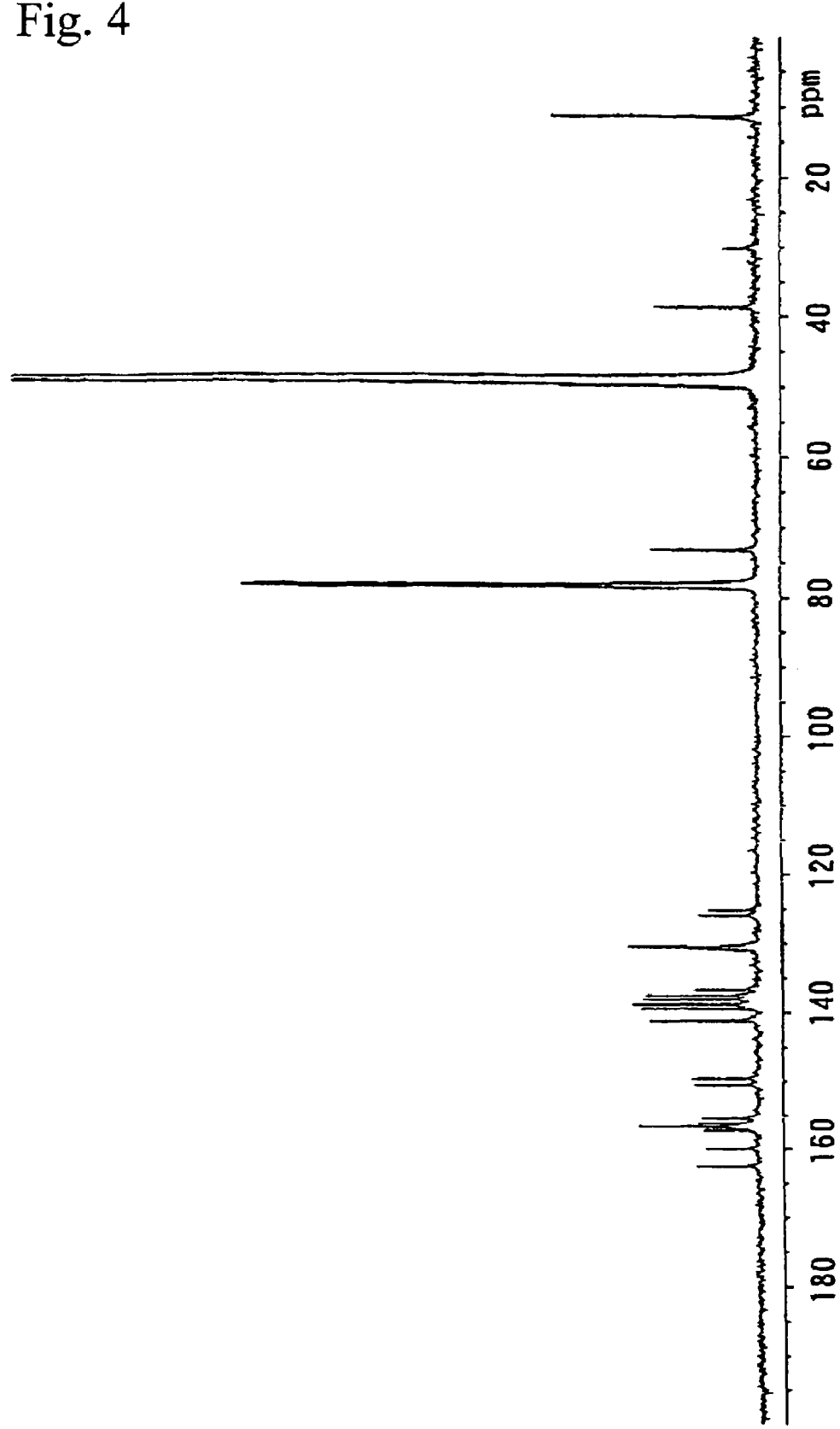
FIG. 4 shows a 125 MHz $^{13}$C-NMR spectrum of the GM-95 substance.

6) Infrared absorption spectrum (FT-IR): as shown in FIG. 2
   vmax ($cm^{-1}$): 3421, 3147, 2958, 2923, 2854, 1733, 1670, 1650, 1544, 1496, 1438, 1392, 1351, 1315, 1267, 1199, 1174, 1118, 1087, 1058, 1033, 975, 943, 929, 914, 883, 798
7) Solubility in solvents: The GM-95 substance is insoluble in water and acetone. It is soluble in a mixture consisting of chloroform and methanol (1:1).
8) Color of the substance: White yellowish powders
9) Nuclear magnetic resonance spectrum The chemical shift of the 500 MHz $^1$H-NMR spectrum (shown in FIG. 3) and that of the 125 MHz $^{13}$C-NMR spectrum (shown in FIG. 4), which were measured at 25° C. in a solution consisting of heavy chloroform and heavy methanol (1:1), are shown below.

Table 4

TABLE 4

| Carbon position | $^{13}$C-NMR | $^1$H-NMR |
|---|---|---|
| 1 | 162.5 | |
| 2 | 150.5 | |
| 3 | 125.1 | |
| 4 | 155.4 | |
| 5 | 149.6 | |
| 6 | 126.0 | |
| 7 | 157.3 | |
| 8 | 137.8 | 8.17(s, 1H) |
| 9 | 130.4 | |
| 10 | 156.8 | |
| 11 | 138.8 | 8.24(s, 1H) |
| 12 | 130.7 | |
| 13 | 156.2 | |

TABLE 4-continued

| Carbon position | $^{13}$C-NMR | $^1$H-NMR |
|---|---|---|
| 14 | 141.2 | 8.00(s, 1H) |
| 15 | 136.7 | |
| 16 | 156.6 | |
| 17 | 139.4 | 8.28(s, 1H) |
| 18 | 130.9 | |
| 19 | 156.6 | |
| 20 | 138.1 | 8.18(s, 1H) |
| 21 | 130.4 | |
| 22 | 160.0 | |
| 23 | 38.7 | 3.8(m, 1H), 3.46(m, 1H) |
| 24 | 73.2 | 6.19(br s, 1H) |
| 25 | 11.5 | 2.47(s, 3H) |
| 26 | 11.5 | 2.64(s, 3H) |

10) Retention time (RT) in high performance liquid chromatography (HPLC)

A peak was detected at 6.1 minutes under the following analytical conditions.
Column: PEGASIL ODS (inside diameter 4.6 mm×250 mm, manufactured by Senshu Scientific Co. Ltd.).
Mobile phase: acetonitrile/trifluoroacetic acid/water (70:0.1:30 V/V/V)
Flow rate: 1 ml/min.
Detection: 254 nm Based in the above-described physicochemical data, the GM-95 substance was identified as having the following chemical structure.

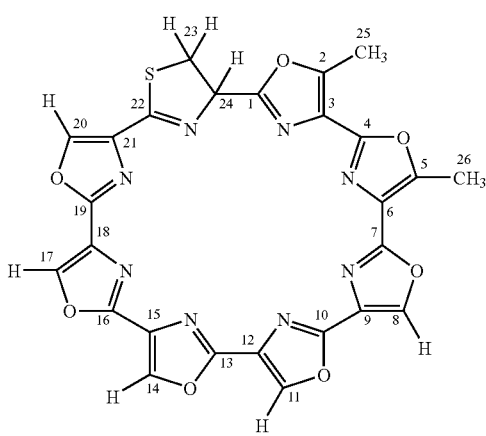

(1)

EXAMPLE 2

Pharmacological Test (Antitumor Actions of GM-95 Substance and 5-Fluorouracil)

The tumor cells described in Table 5 were suspended in 10% fetal bovine serum-added RPMI1640 medium, and the medium containing the cells were then inoculated into a culture plate (38 mm) at a concentration of $2 \times 10^3$ cells. Thereafter, the cells were cultured overnight in a $CO_2$ incubator under conditions consisting of 37° C. and 15% $CO_2$. Thereafter, test agents (GM-95 substance and 5-fluorouracil) that had been diluted to various concentrations were added to the 10% fetal bovine serum-added RPMI1640 medium, and the obtained mixtures were further cultured for 72 hours. After completion of the culture, the cells were fixed with 25% glutaraldehyde for 15 minutes, and they were then washed with water 3 times. Subsequently, the cells were stained with 0.05% crystal violet that had been diluted with a 20% aqueous methanol solution, and they were then washed with water 3 times and then dried. The crystal violet was extracted with 100 μl of 0.05 M sodium dihydrogen phosphate/ethanol (1/1 (v/v)), and the absorbance at 540 nm was measured with an automatic spectroscope. IC50 was defined as a concentration necessary for reducing 50% of the absorbance of a control. The results are shown below.

Table 5

TABLE 5

| Cell strain (Origin) | GM-95 | 5-Fluorouracil |
|---|---|---|
| OVCAR-3 (Human ovarian cancer) | 3.41 | 0.37 |
| PC-3 (Human prostatic cancer) | 8.82 | 5.7 |
| SKOV-3 (Human ovarian cancer) | 3.73 | 7.84 |
| MCF-7 ((Human breast cancer) | 7.73 | 1.12 |
| ZR75-1 (Human breast cancer) | 4.04 | 3.63 |
| PAN-3 (Human pancreatic cancer) | 7.09 | 8.82 |
| KM12C-SM (Human colon cancer) | 3.74 | 1.32 |
| A375SM (Human melanoma) | 7.04 | 2.89 |
| TMK-1 (Human stomach cancer) | 3.75 | 0.33 |
| HT-29 (Human colon cancer) | 7.1 | 2.1 |
| DLD-1 (Human colon cancer) | 6.2 | 5.5 |
| Renca (Mouse kidney cancer) | 0.97 | 0.58 |

Concentration necessary for inhibiting 50% of growth of various types of tumor cells ($IC_{50}$ μM)

The compound of the present invention was able to inhibit the growth of various types of tumor cells in vitro.

EXAMPLE 3

Effects of Combined Use of GM-95 Substance (Telomestatin) and Another Antitumor Substance Antitumor Substances As antitumor substances that were used in combination with the GM-95 substance, Etoposide (ETP; manufactured by Bristol-Myers Squibb), Cisplatin (cDDP; manufactured by Bristol-Myers Squibb), Adriamycin (ADM; manufactured by SIGMA), and Camptothecin (CTP; manufactured by SIGMA) were used.

Tumor Cells

As tumor cells, MCF-7 cells (breast cancer; ATCC HTB-22), SKOV-3 cells (ovarian cancer), HT-29 cells (colon cancer), and HT1080 cells (sarcoma; ATCC CRL-12012) were used. Each type of cells had been furnished from Tsuruo Laboratory, Institute of Molecular and Cellular Biosciences, the University of Tokyo. MCF-7 cells were cultured in a medium formed by adding 10% FCS, 200,000 U/L penicillin, and 100 mg/L streptomycin to a DMEM medium (manufactured by SIGMA). SKOV-3 cells, HT1080 cells, and HT-29 cells were cultured in a medium formed by adding 10% FCS, 200,000 U/L penicillin, and 100 mg/L streptomycin to an RPMI1640 medium (manufactured by SIGMA).

Figure 5:
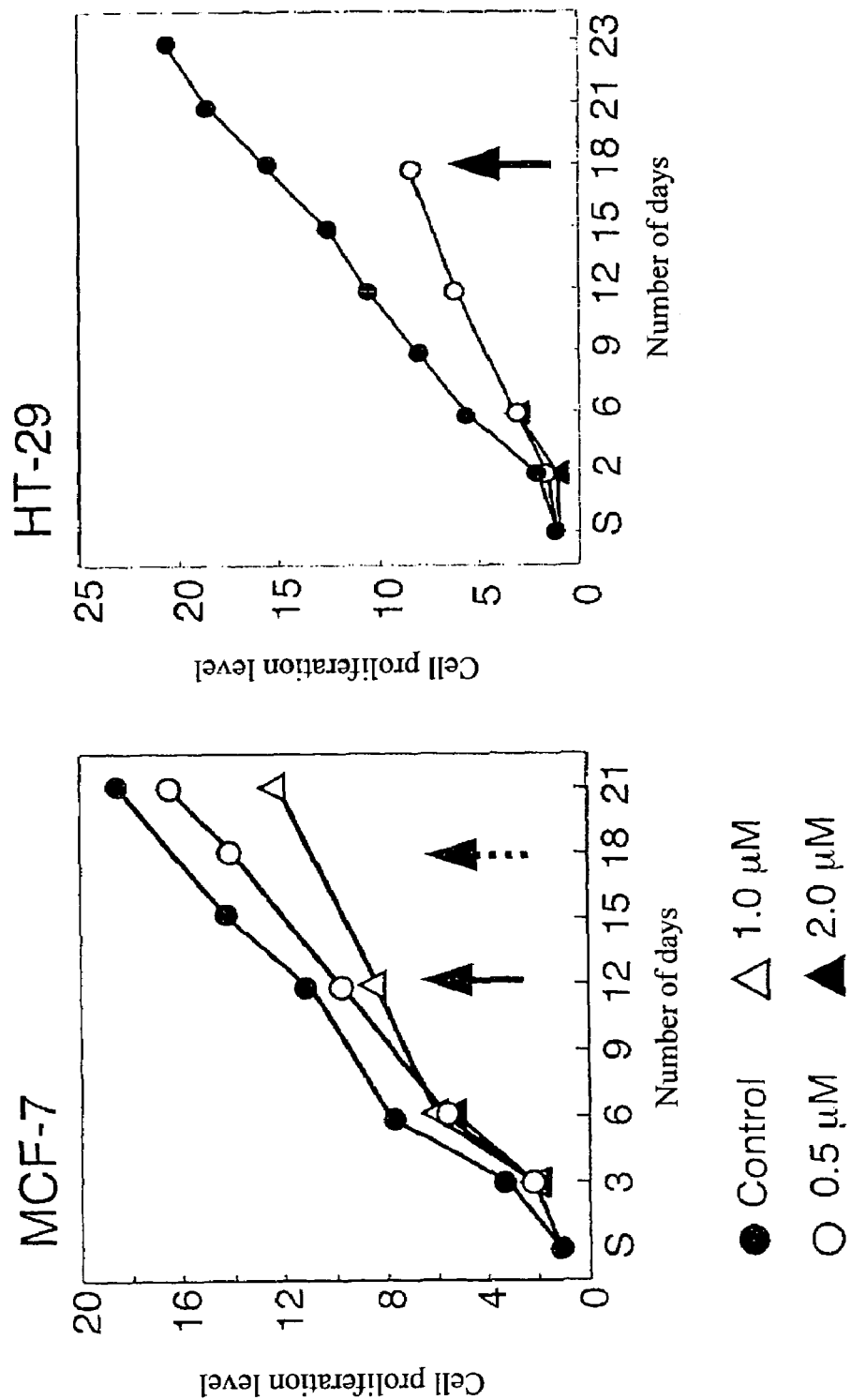
FIG. 5 shows a growth curve (PDL) of MCF-7 cells and that of HT-29 cells, which were measured in Example 3.
Figure 6:
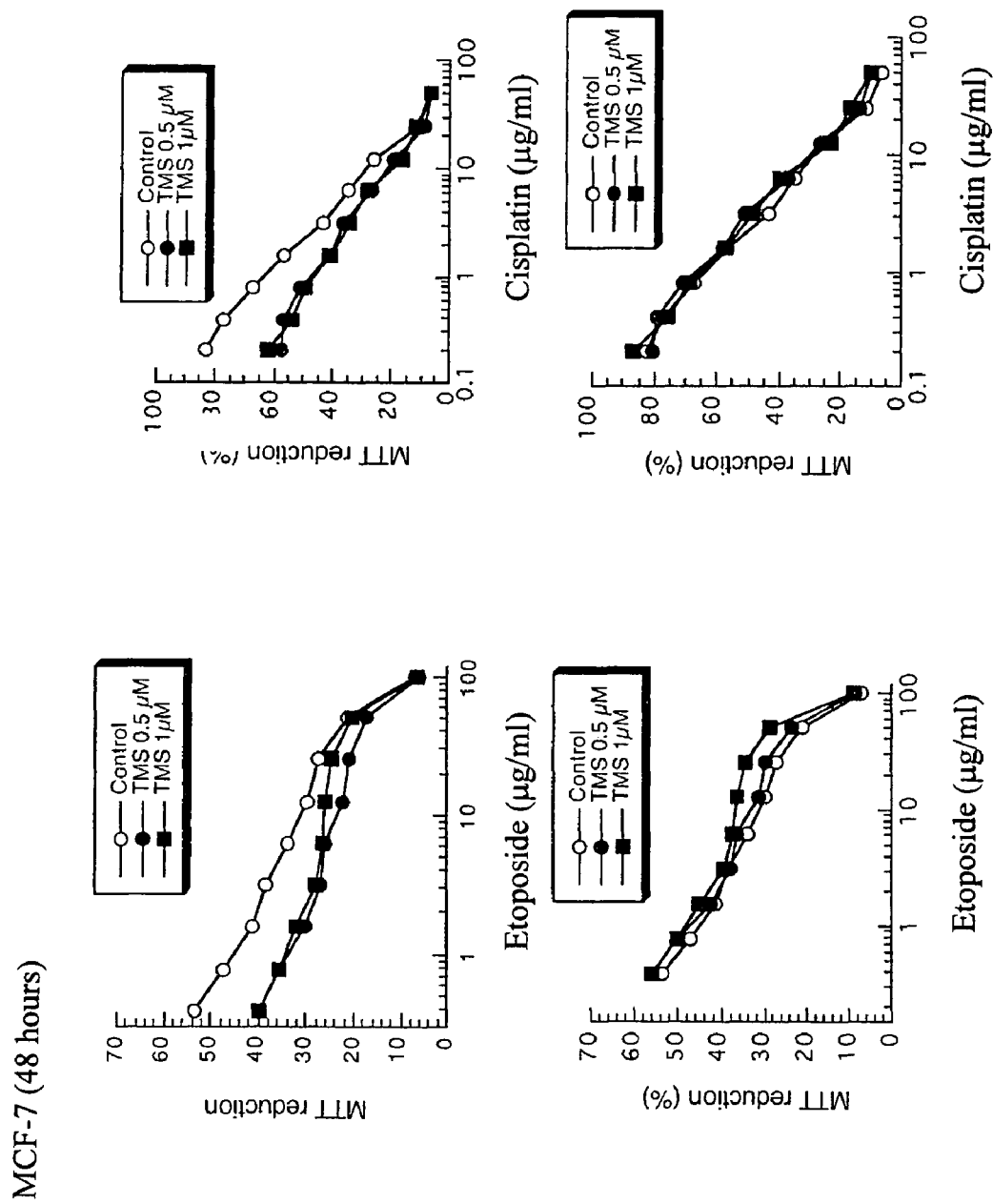
FIG. 6 includes graphs showing the results obtained by measuring the number of surviving cells according to the MTT method, after MCF-7 cells were cultured for 48 hours in the presence of the GM-95 substance and Etoposide or Cisplatin.
Figure 7:
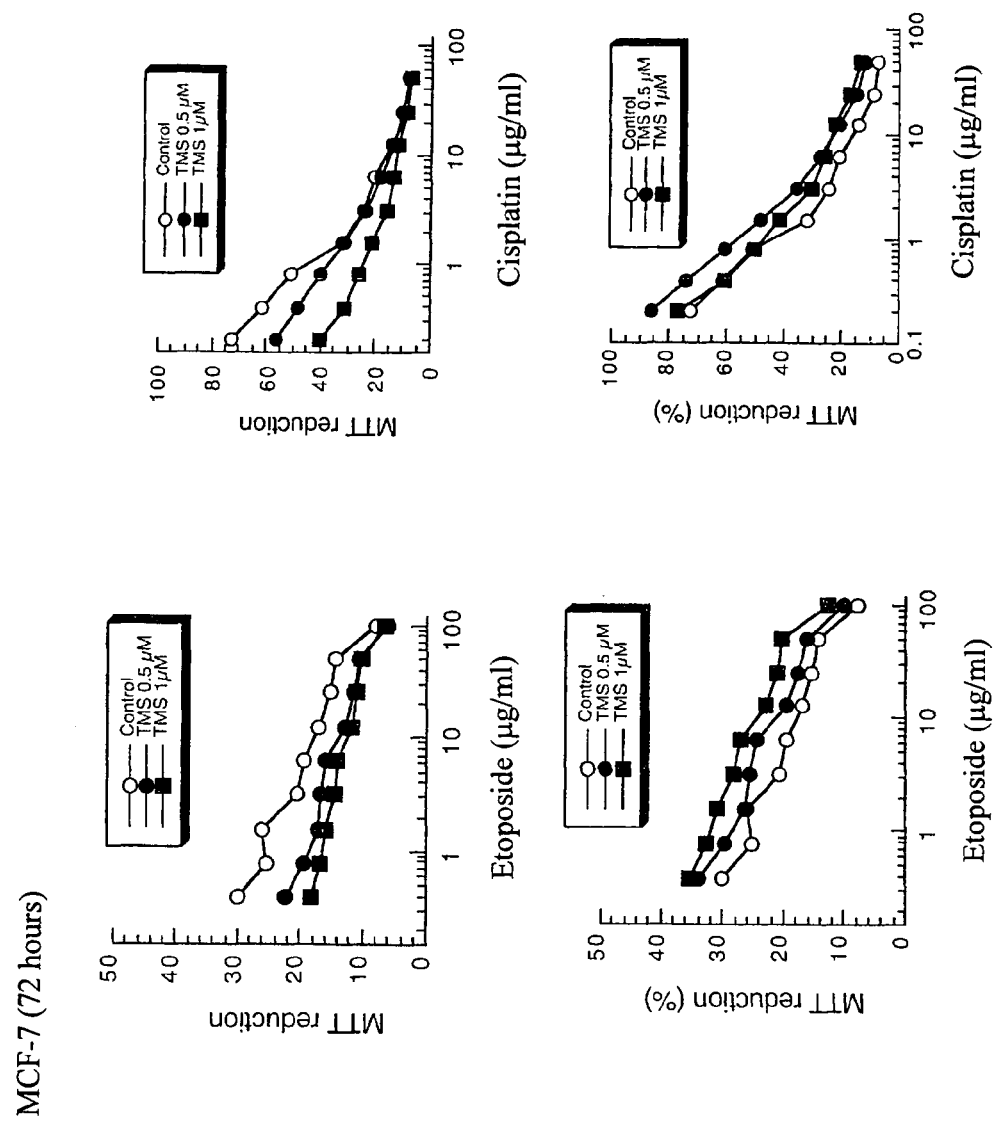
FIG. 7 includes graphs showing the results obtained by measuring the number of surviving cells according to the MTT method, after MCF-7 cells were cultured for 72 hours in the presence of the GM-95 substance and Etoposide or Cisplatin.
Figure 8:
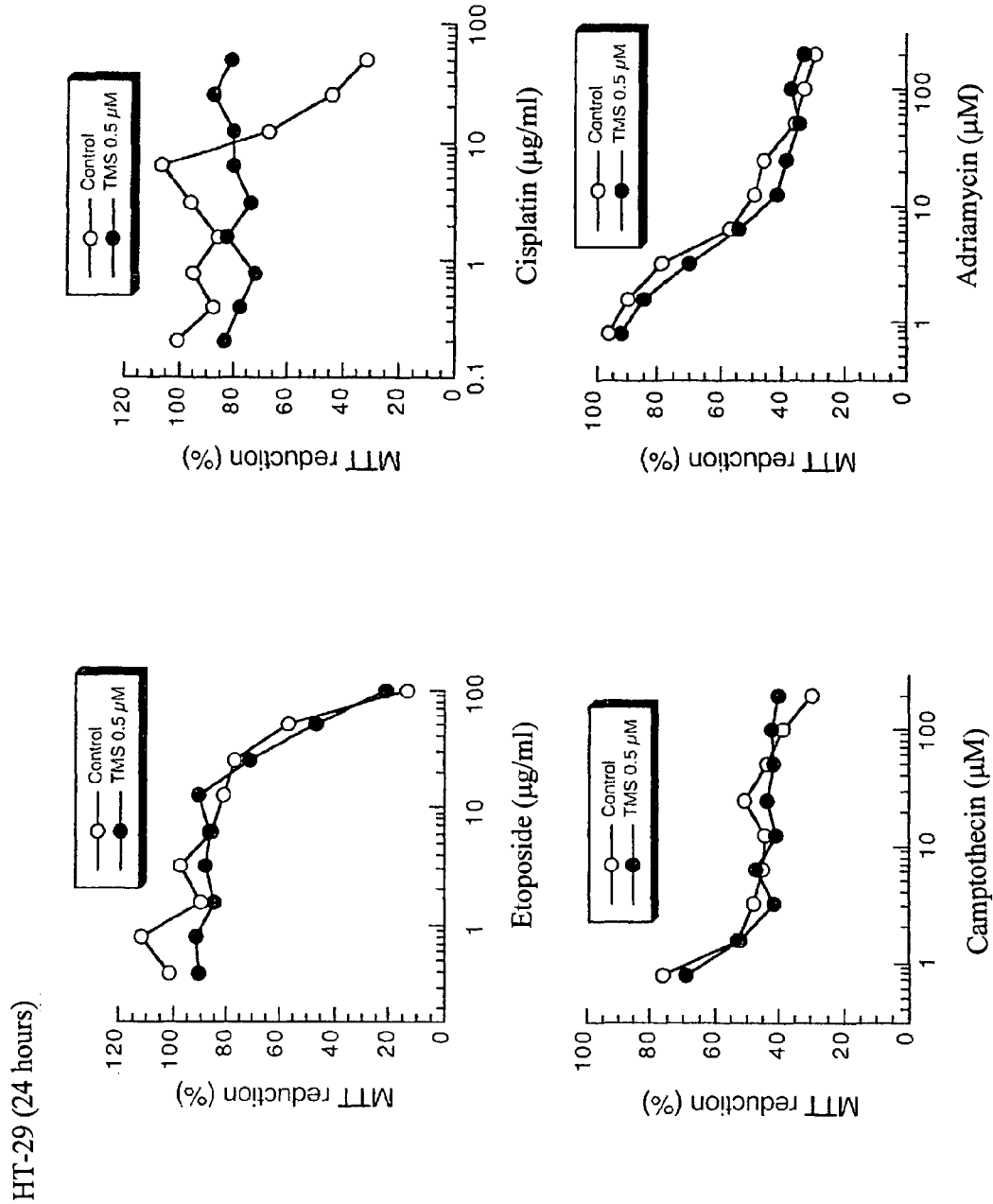
FIG. 8 includes graphs showing the results obtained by measuring the number of surviving cells according to the MTT method, after HT-29 cells were cultured for 24 hours in the presence of the GM-95 substance and Etoposide, Cisplatin, Camptothecin, or Adriamycin.
Figure 9:
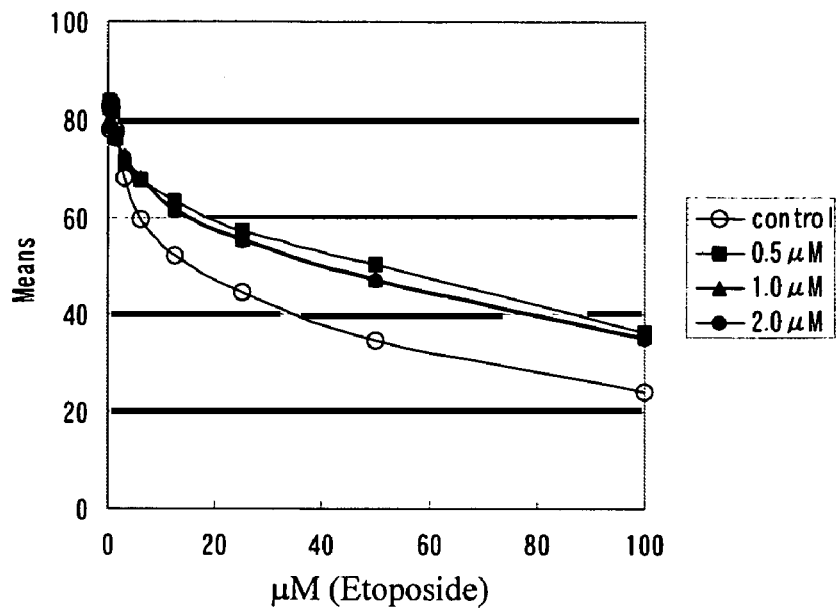
FIG. 9 includes graphs showing the results obtained by measuring the number of surviving cells, after SKOV-3 cells were cultured for 24 hours in the presence of the GM-95 substance and Etoposide or Cisplatin.
Figure 9:
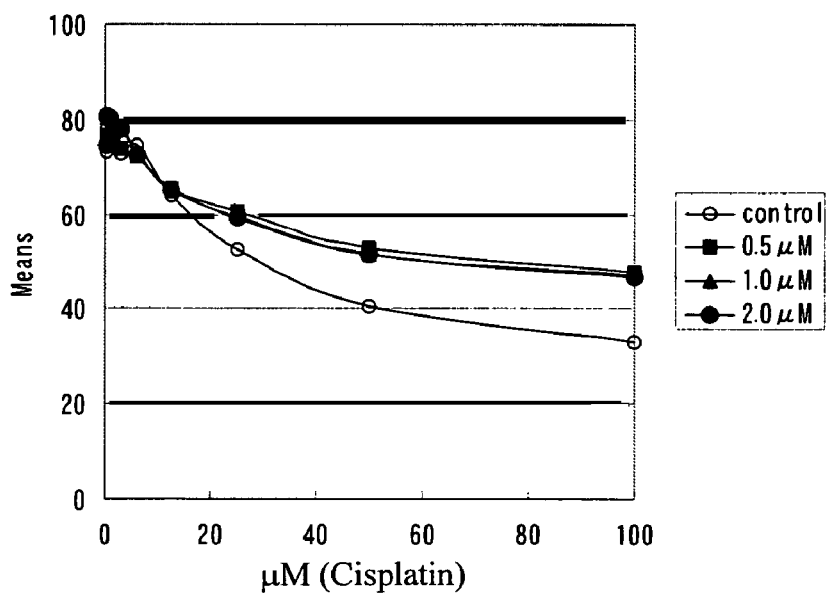
Figure 10:
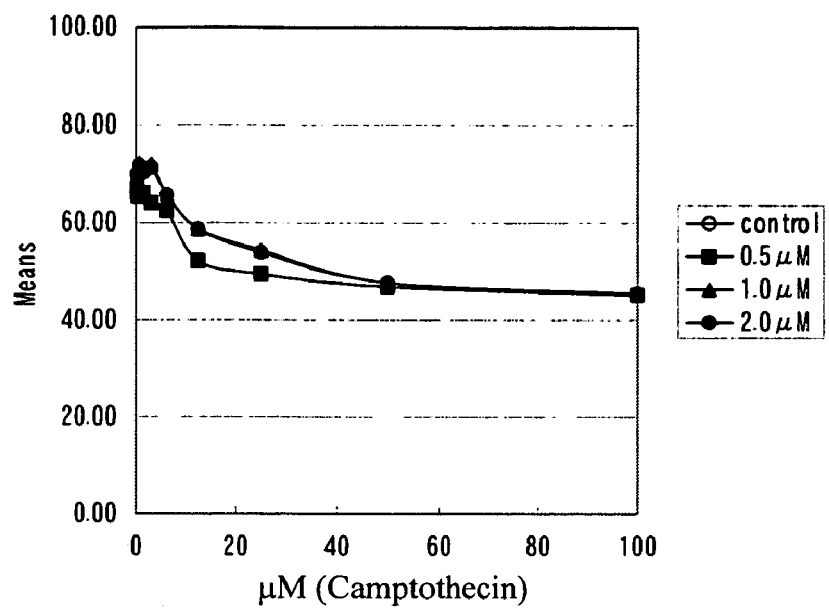
FIG. 10 includes graphs showing the results obtained by measuring the number of surviving cells, after SKOV-3 cells were cultured for 24 hours in the presence of the GM-95 substance and Camptothecin or Adriamycin.
Figure 10:
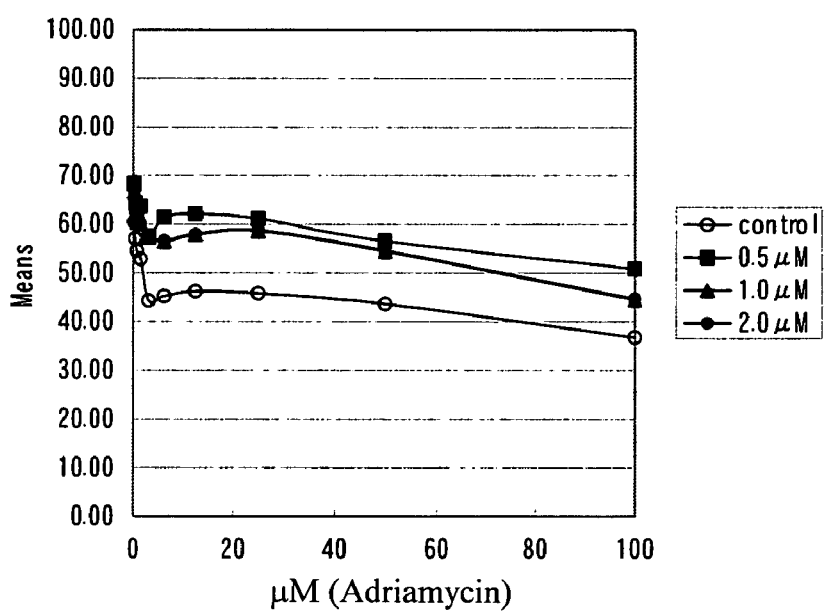
Figure 11:
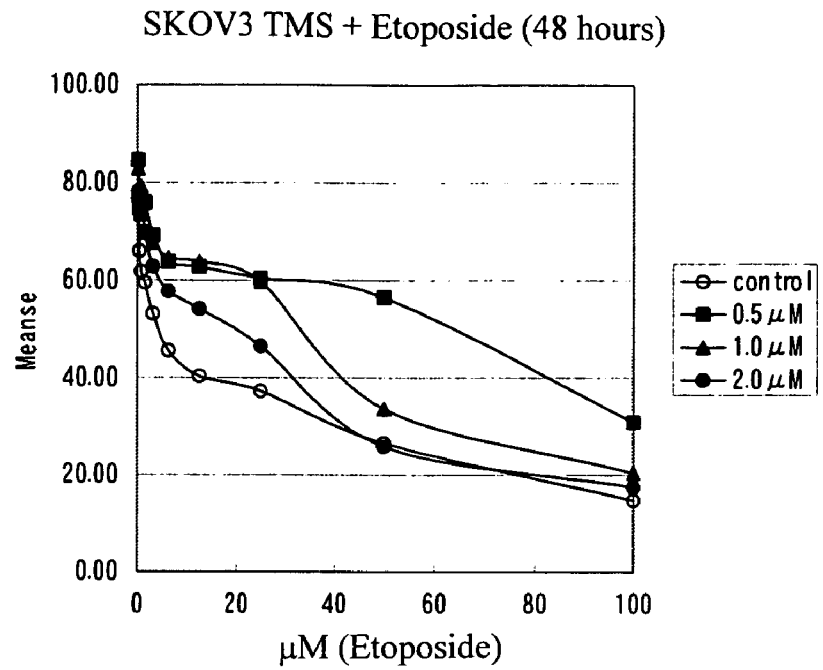
FIG. 11 includes graphs showing the results obtained by measuring the number of surviving cells, after SKOV-3 cells were cultured for 48 hours in the presence of the GM-95 substance and Etoposide or Cisplatin.
Figure 11:
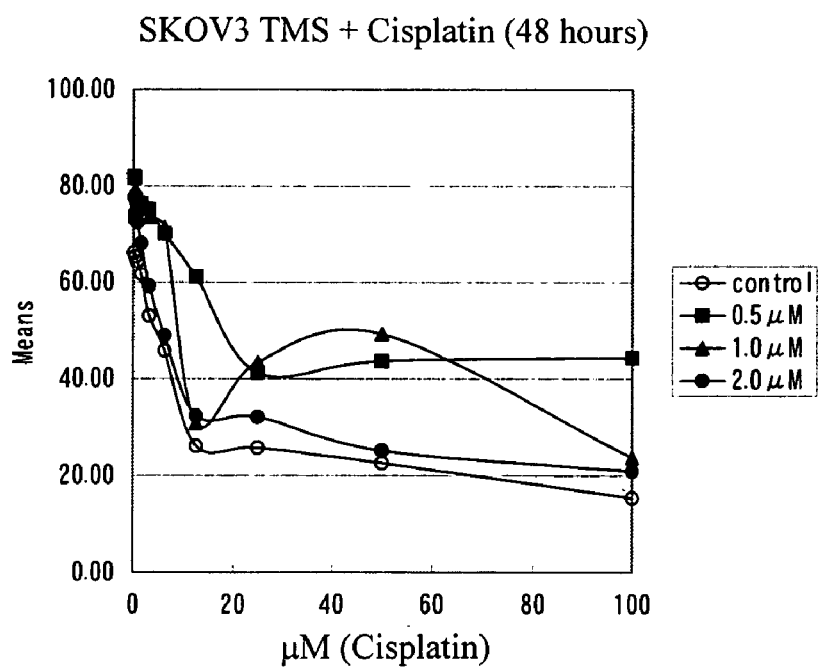
Figure 12:
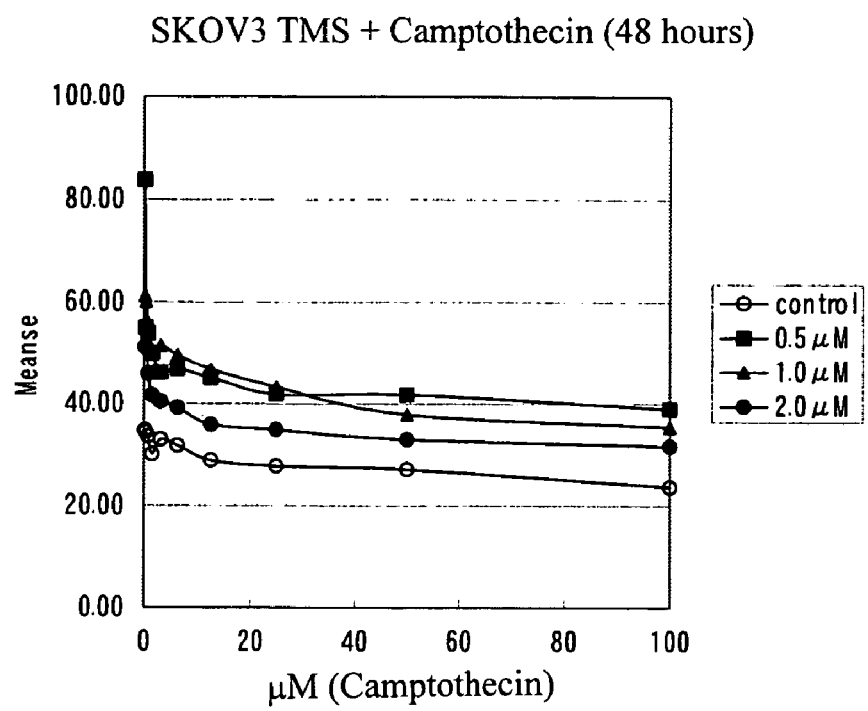
FIG. 12 includes graphs showing the results obtained by measuring the number of surviving cells, after SKOV-3 cells were cultured for 48 hours in the presence of the GM-95 substance and Camptothecin or Adriamycin.
Figure 12:
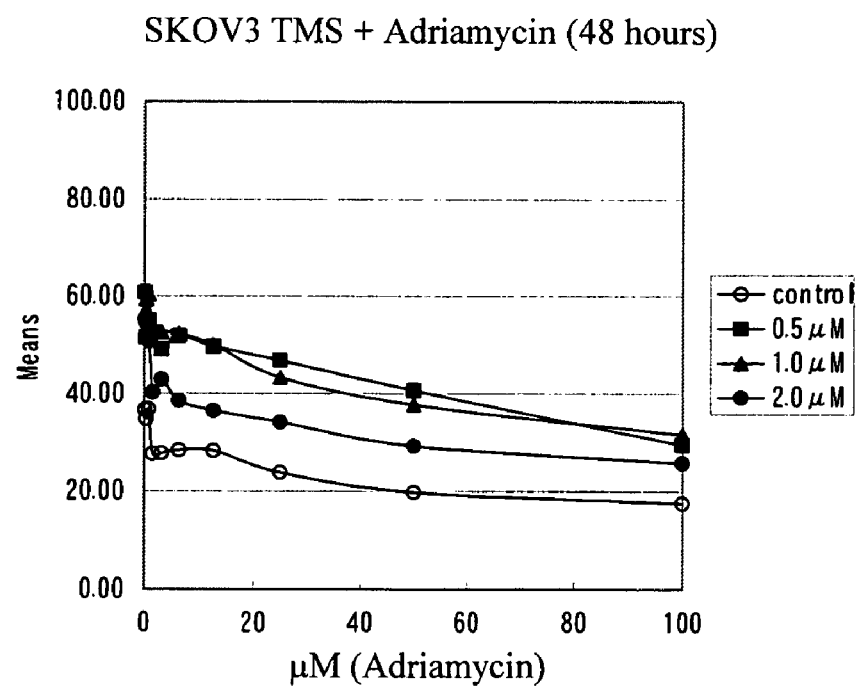
Figure 13:
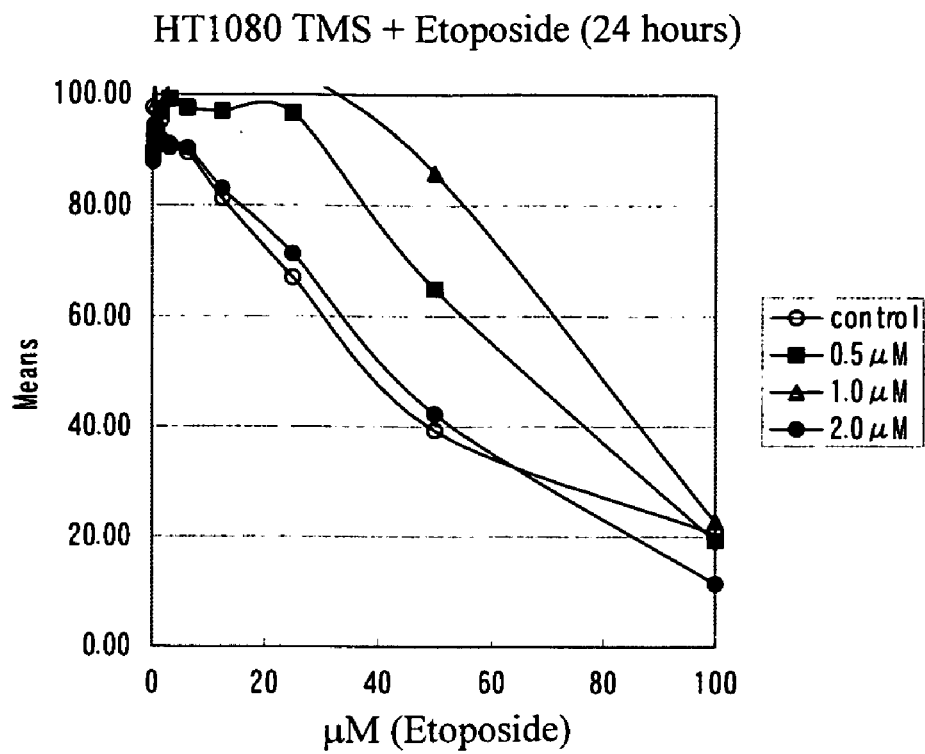
FIG. 13 includes graphs showing the results obtained by measuring the number of surviving cells, after HT1080 cells were cultured for 24 hours in the presence of the GM-95 substance and Etoposide or Cisplatin.
Figure 13:
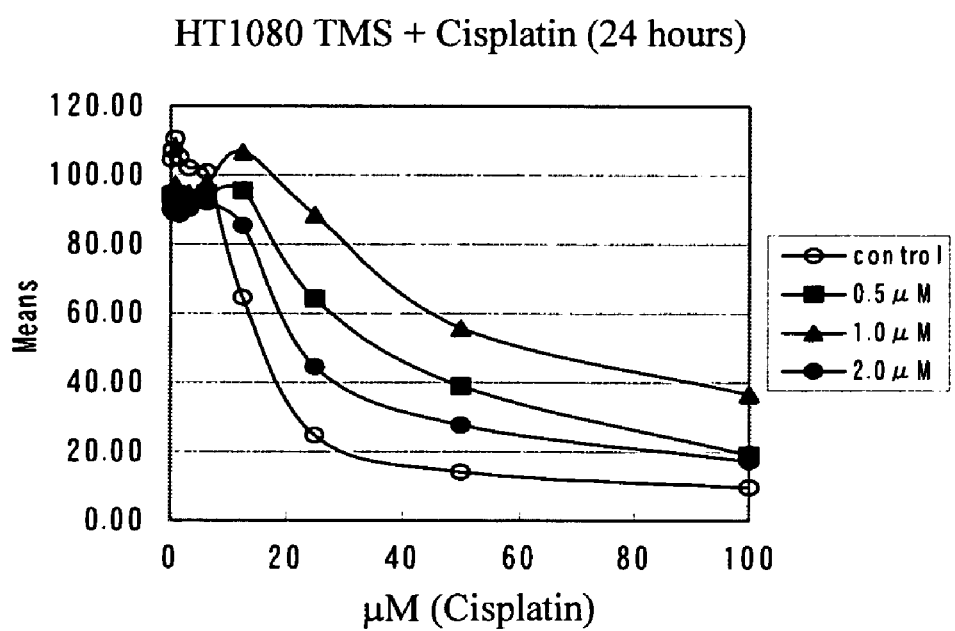
Figure 14:
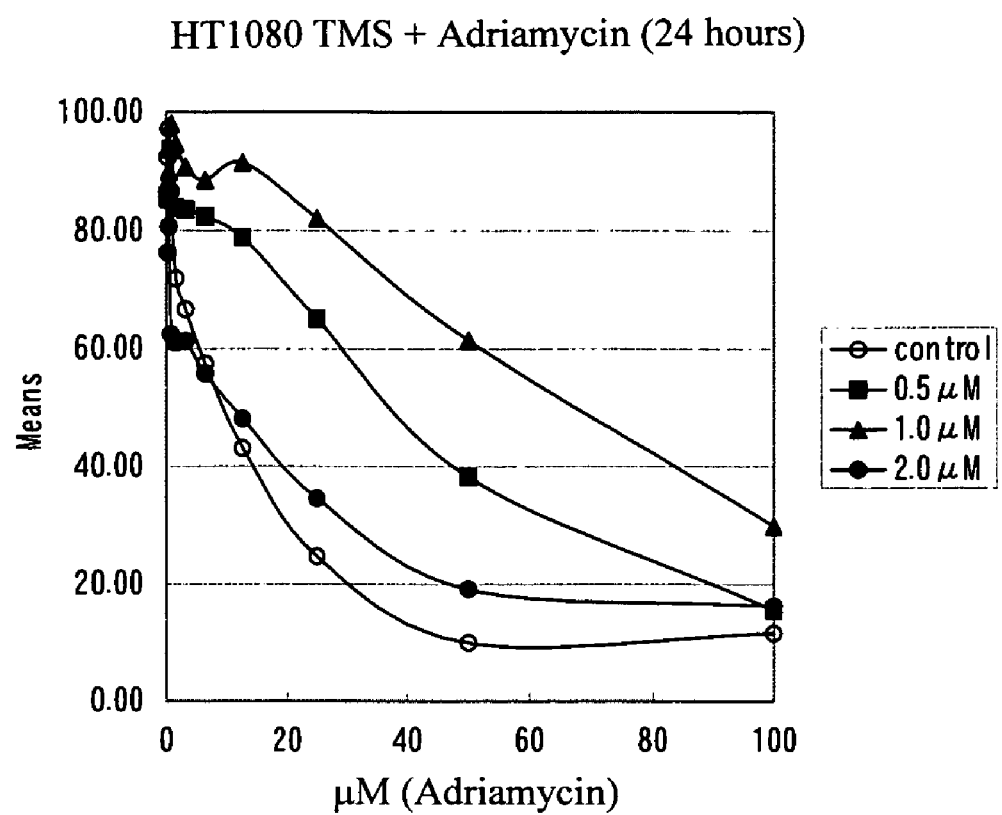
FIG. 14 includes graphs showing the results obtained by measuring the number of surviving cells, after HT1080 cells were cultured for 24 hours in the presence of the GM-95 substance and Adriamycin.
Figure 15:
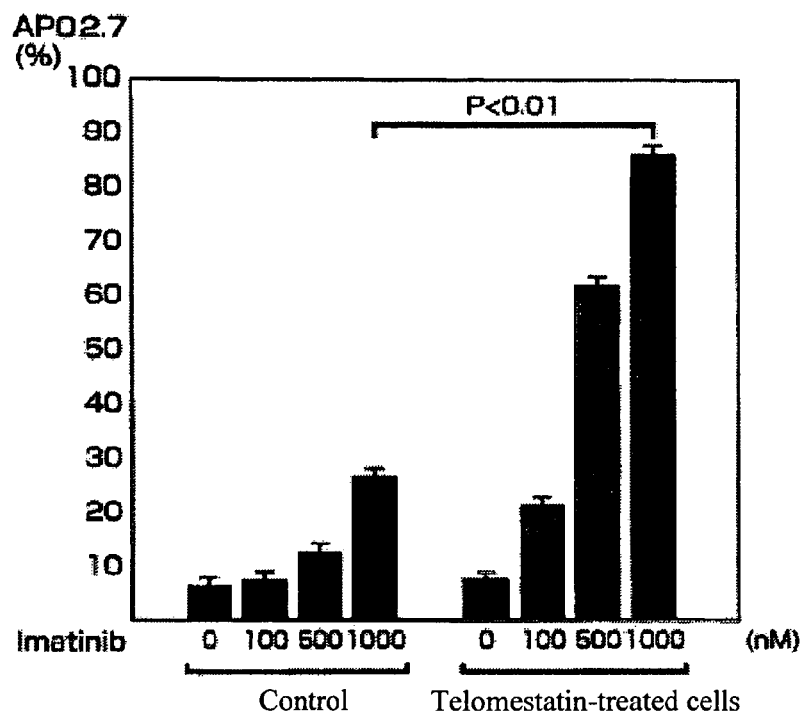
FIG. 15 is a graph showing the measurement results of apoptosis induction into K562 cells by the combined use of the GM-95 substance and Imanitib.
Figure 16:
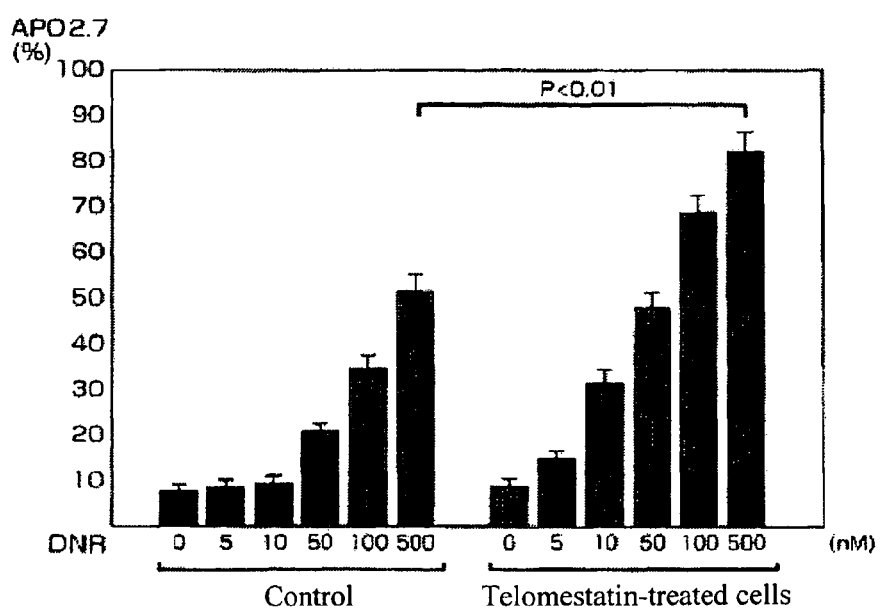
FIG. 16 is a graph showing the measurement results of apoptosis induction into K562 cells by the combined use of the GM-95 substance and Daunorubicin (DNR)
Figure 17:
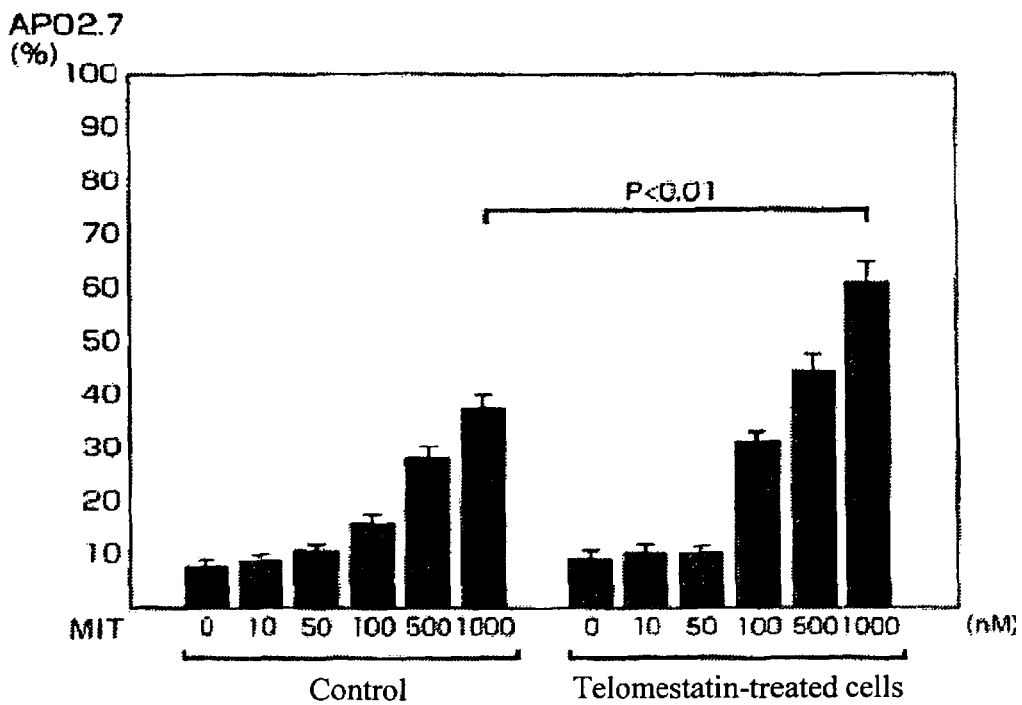
FIG. 17 is a graph showing the measurement results of apoptosis induction into K562 cells by the combined use of the GM-95 substance and Mitoxantrone (MIT)
Figure 18:
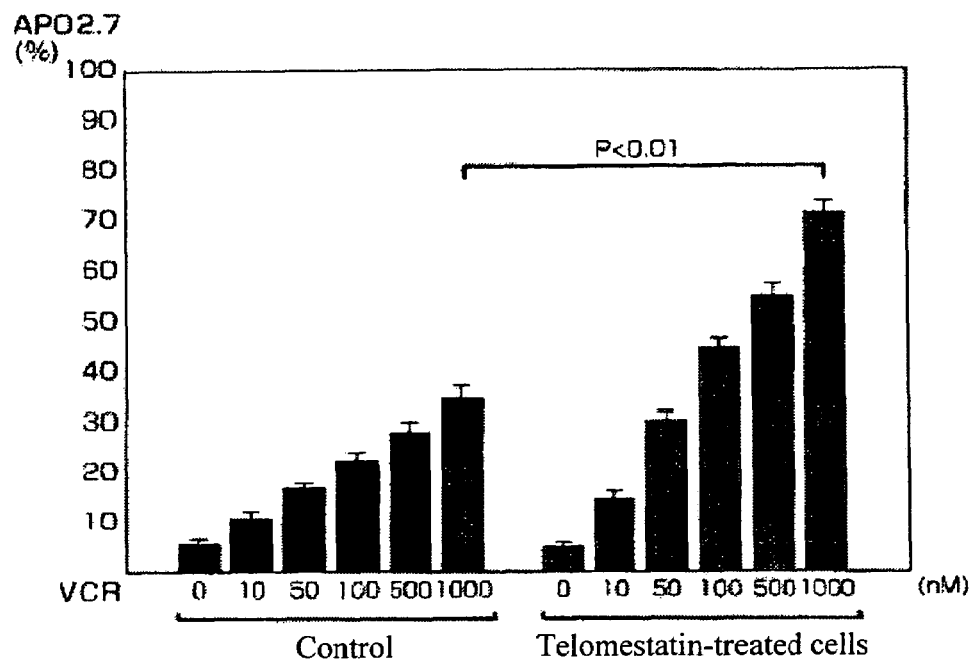
FIG. 18 is a graph showing the measurement results of apoptosis induction into K562 cells by the combined use of the GM-95 substance and Vincristine (VCR)

Long-Term Culture of Tumor Cells in the Presence of GM-95 Substance and Another Antitumor Substance The aforementioned cells were prepared to a concentration of $5 \times 10^4$ cells/ml. They were then added to a 12-well plate or a 6-well plate (both of which are manufactured by Sumitomo Bakelite Co., Ltd.) in amounts of 500 μl and 1 ml, respectively. The GM-95 substance was added to the above cells to final concentrations of 2.0 μM, 1.0 μM, and 0.5 μM, and they were then cultured until they became confluent. When the cells were subjected to subculture, the number of cells in each treated group was counted, and the growth curves (PDL) were prepared (FIG. 5). Since each type of cells has different sensitivity to the GM-95 substance, the cells were recovered every week, the length of a telomere was measured, and the effects obtained by the combined use of the GM-95 substance with another antitumor substance were studied. In order to examine the effects of such combined use, the treated cells were prepared to a concentration of $5 \times 10^4$ cells/ml, and 100 µl each of the cells was dispersed in a 96-well plate (manufactured by Sumitomo Bakelite Co., Ltd.), followed by incubation for 12 to 15 hours. Thereafter, an antitumor agent comprising the GM-95 substance and each of the aforementioned antitumor substances was added to the cells. A change in the number of surviving cells over time was monitored every 24 hours. Every 24 hours, surviving cells were quantified according to the MTT (3-(4,5-dimethylthiazol-2-yl)-2,5-diphenyl tetrazolium bromide) method. The MTT method was carried out as follows. MTT (manufactured by SIGMA) was adjusted to be 5 g/100 ml by addition of PBS. Thereafter, 10 µl each of MTT was added to each well. The generated formazan was observed with a speculum, and when a sufficient amount of formazan was generated, the medium was aspirated. 100 µl of dimethyl sulfoxide (DMSO) was added to each well, and the mixture was then stirred, followed by colorimetry. Such colorimetry was carried out by measuring the absorbance at 570 nm using ARVO SX (manufactured by Perkin Elmer). The results regarding the effects of the combined use of the GM-95 substance with each of the aforementioned antitumor substances are shown in FIGS. 6 to 14. In the figures, "TMS" represents the GM-95 substance (Telomestatin), and "control" indicates a control substance.

EXAMPLE 4

Apoptosis Induction into K562 Cells by Combined Use of GM-95 Substance with Another Antitumor Substance K562 cells (available from ATCC (Rockville, Md.)) were cultured for 10 days in the presence of 2 µM Telomestatin (GM-95 substance). Subsequently, the Telomestatin-treated K562 cells were incubated for 72 hours together with Imanitib, Daunorubicin (DNR), Mitoxantrone (MIT), or Vincristine (VCR). The expression of apoptosis was measured by flow cytometric analysis using an FITC conjugate APO 2.7 monoclonal antibody (which is generated to a mitochondrial membrane protein (7A6 antigen) and is expressed in cells wherein apoptosis takes place). The results are shown in FIGS. 15 to 18. In the figures, the terms "control," "TMS," "Imanitib," "DNR," "MIT," and "VCR" represent a control substance, the GM-95 substance (Telomestatin), Imanitib, Daunorubicin, Mitoxantrone, and Vincristine, respectively.

Imanitib, Daunorubicin, Mitoxantrone, and Vincristine are antitumor substances, the action mechanisms of which are different from one another. As is clear from the results shown in FIGS. 15 to 18, it is found that when Telomestatin is used in combination of each of these antitumor substances, both substances act synergistically, so that their effects of inducing apoptosis in tumor cells are significantly improved.

EXAMPLE 5

Effects of Combined Use of GM-95 Substance with Another Antitumor Substance (HT1080 Cells)

Tumor cells were cultured under the conditions described below using the GM-95 substance and another antitumor substance in the same manner as in Example 3. After a certain period of time had passed, the survival rate of the tumor cells was measured.

Antitumor Substances

The following antitumor substances were used in combination with the GM-95 substance:

Doxorubicin hydrochloride (DDP) (Wako Pure Chemical Industries, Ltd., No. 040-21521);

5-Fluorouracil (5-FU) (Wako Pure Chemical Industries, Ltd., No. 064-01403);

Cis-diammine-dichloro platinum (III) (CTP) (Wako Pure Chemical Industries, Ltd., No. 047-22511); and Etoposide phosphate (ETP) (Wako Pure Chemical Industries, Ltd., No. 058-06341).

Tumor Cells

HT1080 cells were used as tumor cells. In the following experiments, the tumor cells were cultured in a medium formed by adding 10% FBS to RPMI1640 (SIGMA, R8758) using a $CO_2$ incubator (temperature: 37° C.; humidity: 100%; $CO_2$ concentration: 5%).

Experimental Methods

HT1080 cells were cultured under conditions described in the following (A) to (C). After completion of the culture, the survival rate of the tumor cells was measured by the MTT method.

(A): 0.5 µM GM-95 substance and each of the aforementioned antitumor substances with a certain concentration were simultaneously added to the HT1080 cells, and the tumor cells were then cultured for 2 days. After completion of the culture, the survival rate of the tumor cells was measured.

(B): The tumor cells were previously cultured for 7 days together with 0.5 µM or 1 µM GM-95 substance. Thereafter, each of the aforementioned antitumor substances with a certain concentration was added to the cells in the absence of the GM-95 substance, followed by culture for 2 days. After completion of the culture, the survival rate of the tumor cells was measured.

(C): The tumor cells were previously cultured for 7 or 14 days together with 0.5 µM or 1 µM GM-95 substance. Thereafter, each of the aforementioned antitumor substances with a certain concentration was added to the cells in the presence of the GM-95 substance, followed by culture for 2 days. After completion of the culture, the survival rate of the tumor cells was measured. (It is to be noted that the survival rate of the tumor cell group that had been cultured for 14 days in the presence of 1 µM GM-95 substance could not be measured because the number of surviving cells was very small.)

Results

Figure 19:
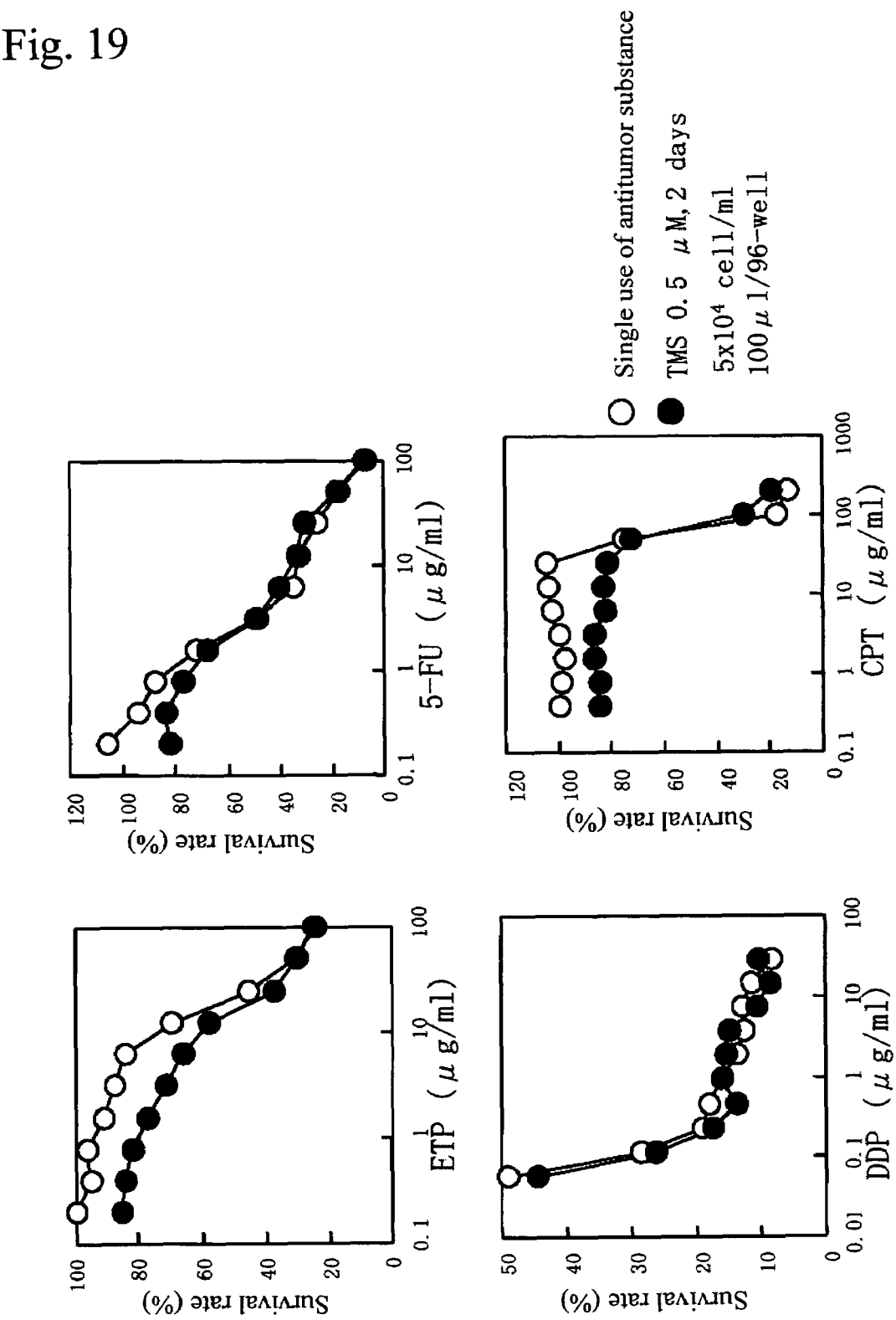
FIG. 19 includes graphs showing the results of Example 5(A)
Figure 20:
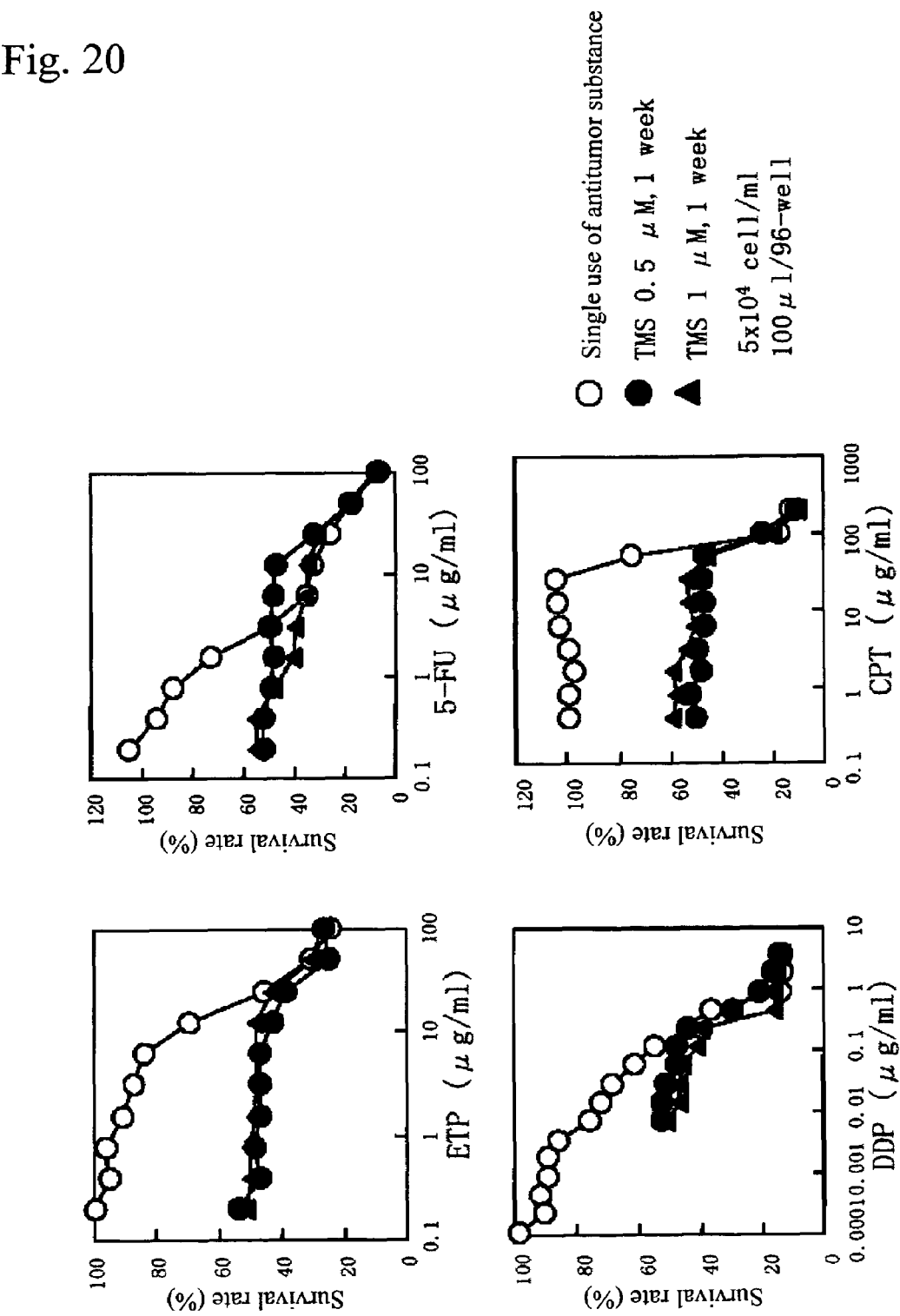
FIG. 20 includes graphs showing the results of Example 5(B)
Figure 21:
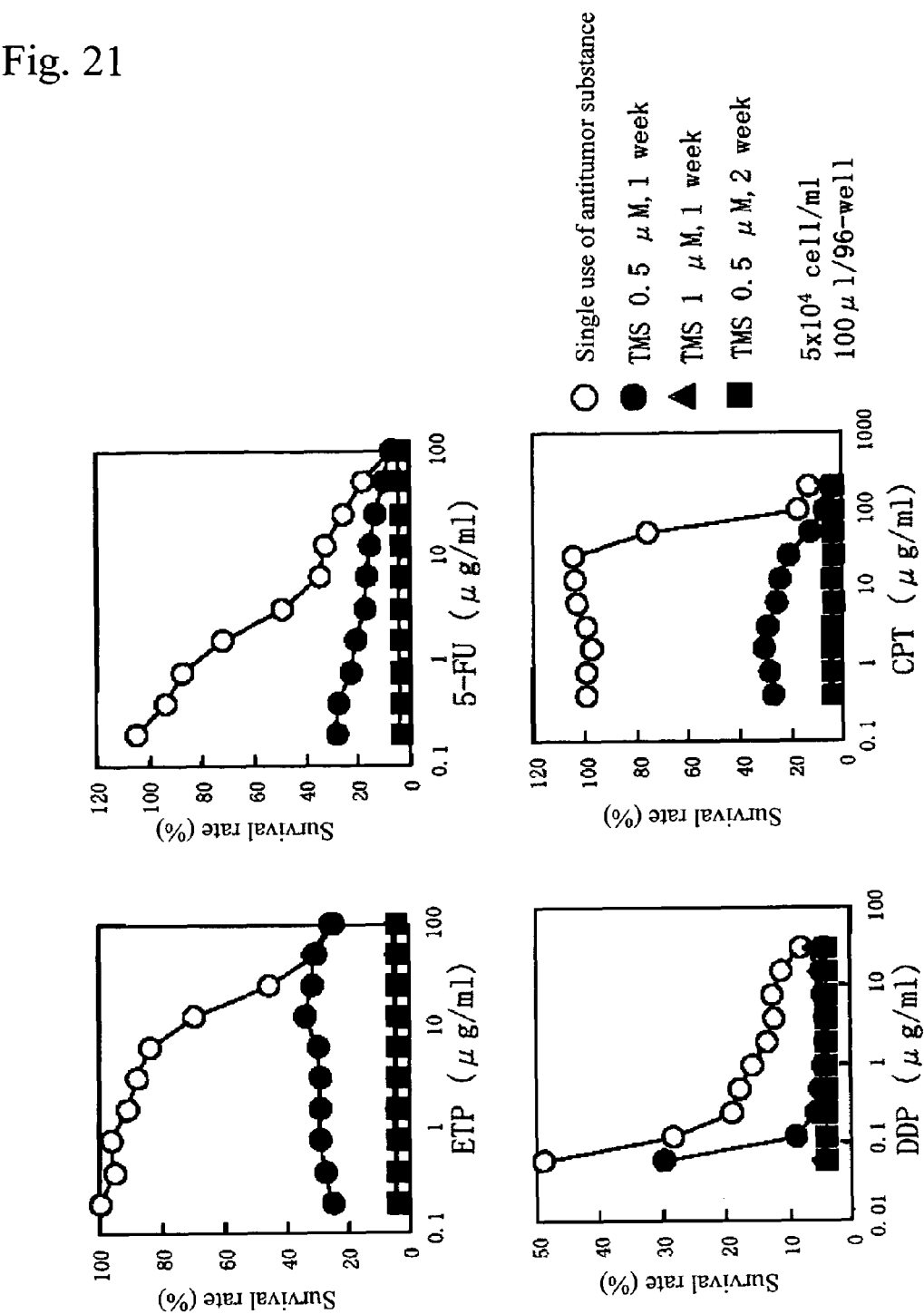
FIG. 21 includes graphs showing the results of Example 5(C)

The results of the aforementioned experiments (A) to (C) are shown in FIGS. 19 to 21, respectively. As shown in FIGS. 19 to 21, it is found that the antitumor action is enhanced by the combined use of the GM-95 substance with another antitumor substance (in both cases of the simultaneous combined use and the successive combined use). In particular, as in the case of (B) and (C), when the tumor cells had previously been treated with the GM-95 substance (0.5 µM or 1 µM) for 7 or 14 days, the effects obtained by the combined use of the GM-95 substance with various types of antitumor substances was significant either in the presence or absence of the GM-95 substance. In addition, even though the concentration of the antitumor substance used in combination with the GM-95 substance was extremely low, excellent effects were exhibited by such combined use (FIGS. 20 and 21). In FIGS. 19 to 21, ○ represents the results obtained when the aforementioned antitumor substance was used singly.

EXAMPLE 6

Effects of Combined Use of Gm-95 Substance with Another Antitumor Substance (MCF-7 Cells)

Tumor cells were cultured under the conditions described below using the GM-95 substance and another antitumor substance in the same manner as in Example 5. After a certain period of time had passed, the survival rate of the tumor cells was measured.

Antitumor Substances

The following antitumor substances were used in combination with the GM-95 substance:
Doxorubicin hydrochloride (DDP) (Wako Pure Chemical Industries, Ltd., No. 040-21521);
5-fluorouracil (5-FU) (Wako Pure Chemical Industries, Ltd., No. 064-01403);
Cis-diammine-dichloro platinum (III) (CTP) (Wako Pure Chemical Industries, Ltd., No. 047-22511); and
Etoposide phosphate (ETP) (Wako Pure Chemical Industries, Ltd., No. 058-06341).

Tumor Cells

MCF-7 cells were used as tumor cells. In the following experiments, the tumor cells were cultured in a medium formed by adding 10% FBS to DMEM (SIGMA, D6046) using a $CO_2$ incubator (temperature: 37° C.; humidity: 100%; $CO_2$ concentration: 5%).

Experimental Methods

MCF-7 cells were cultured under conditions described in the following (D) and (E). After completion of the culture, the survival rate of the tumor cells was measured by the MTT method.
(D): The tumor cells were previously cultured for 7 days together with 1 µM or 2 µM GM-95 substance. Thereafter, each of the aforementioned antitumor substances with a certain concentration was added to the cells in the absence of the GM-95 substance, followed by culture for 2 days. After completion of the culture, the survival rate of the tumor cells was measured.
(E): The tumor cells were previously cultured for 14 days together with 1 µM or 2 µM GM-95 substance. Thereafter, each of the aforementioned antitumor substances with a certain concentration was added to the cells in the absence of the GM-95 substance, followed by culture for 2 days. After completion of the culture, the survival rate of the tumor cells was measured.

Results

Figure 22:
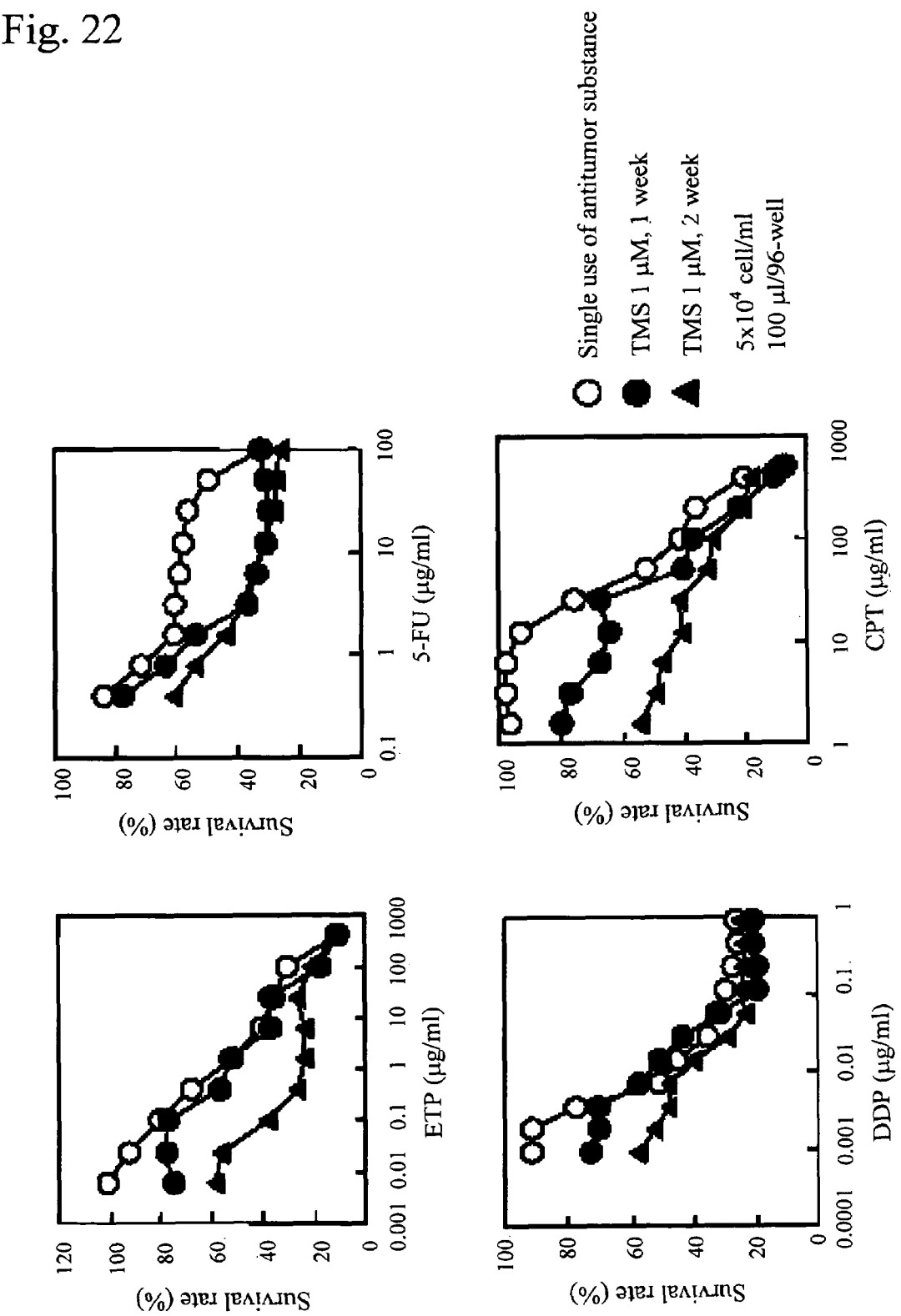
FIG. 22 includes graphs showing the results of Example 6(D).

The results of the aforementioned experiments (D) and (E) are shown in FIG. 22. As shown in FIG. 22, in the case of MCF-7 cells also, it was shown that the antitumor action is enhanced, when the tumor cells were treated with the GM-95 substance (1 µM or 2 µM) for 7 or 14 days and the aforementioned antitumor substance is then used for the cells in the presence or absence of the GM-95 substance. In FIG. 22, ○ represents the results obtained when the aforementioned antitumor substance was used singly.

PREPARATION EXAMPLE 1

Injection

An injection can be prepared at the following mixing ratio according to a common method:

| | |
|---|---|
| GM-95 substance | 5 mg |
| Cisplatin | 5 mg |
| Distilled water used for injection | 5 ml |

All publications, patents and patent applications cited herein are incorporated herein by reference in their entirety.

INDUSTRIAL APPLICABILITY

The combined preparation of the present invention using GM-95 (Telomestatin) is particularly useful as an antitumor agent.

In the antitumor effect enhancer, combined antitumor preparation, or antitumor agent of the present invention, by using the GM-95 substance in combination with another antitumor substance, the antitumor effects of the above antitumor substance is enhanced, or both their antitumor effects act synergistically. Thus, the obtained antitumor activity becomes significantly higher than that obtained when such substances are used singly. In addition, it becomes also possible to administer the agent at a low dosage, and thus it is excellent in terms of safety.

The invention claimed is:

1. A method for enhancing an antitumor effect of an antitumor substance on cancer cells comprising administrating a compound of the following formula (1) or a pharmaceutically acceptable salt thereof in combination with the antitumor substance to the cancer cells, wherein said antitumor substance is different from said compound of the following formula (1) or a pharmaceutically acceptable salt thereof:

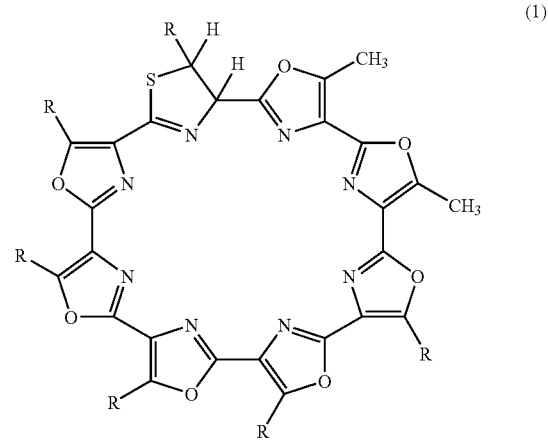

(1)

wherein each R represents a hydrogen atom, and
wherein said antitumor substance is selected from the group consisting of a pyrimidine compound, an anthracycline compound, a vinca alkaloid, a topoisomerase type II inhibitor, and Cisplatin, and
wherein said cancer is selected from the group consisting of stomach cancer, colon cancer, pancreatic cancer, ovarian cancer, prostatic cancer, osteosarcoma and/or soft part sarcoma, skin cancer, and leukemia.

2. The method according to claim 1, wherein said compound of formula (1) or a pharmaceutically acceptable salt thereof is administered prior to administration of said antitumor substance.

3. The method according to claim 1, wherein said compound of formula (1) or a pharmaceutically acceptable salt thereof is administered simultaneously with said antitumor substance.

4. A method for treatment of cancer in a patient comprising administrating a compound of the following formula (1) or a pharmaceutically acceptable salt thereof in combination with an antitumor substance to the patient, wherein said antitumor substance is different from said compound of the following formula (1) or a pharmaceutically acceptable salt thereof:

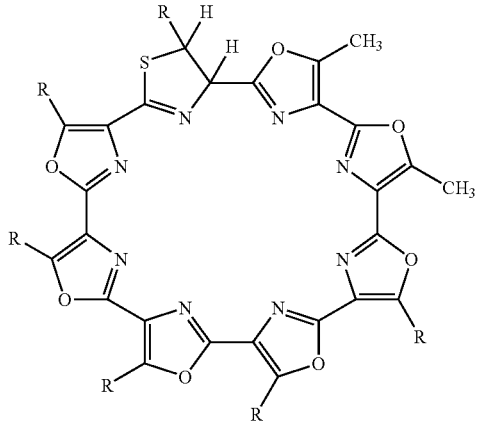
(1)

wherein each R represents a hydrogen atom, and wherein said antitumor substance is selected from the group consisting of a pyrimidine compound, an anthracycline compound, a vinca alkaloid, a topoisomerase type II inhibitor and Cisplatin, and wherein said cancer is selected from the group consisting of stomach cancer, colon cancer, pancreatic cancer, ovarian cancer, prostatic cancer, osteosarcoma and/or soft part sarcoma, skin cancer, and leukemia.

5. The method according to claim 4, wherein said compound of formula (1) or a pharmaceutically acceptable salt thereof is administered prior to administration of said antitumor substance.

6. The method according to claim 4, wherein said compound of formula (1) or a pharmaceutically acceptable salt thereof is administered simultaneously with said antitumor substance.

* * * * *